(12) United States Patent
Gill et al.

(10) Patent No.: US 12,339,274 B2
(45) Date of Patent: Jun. 24, 2025

(54) BLOOD COAGULOMETER AND METHOD

(71) Applicant: The Board of Regents of The University of Texas System, Austin, TX (US)

(72) Inventors: Brijesh S. Gill, Houston, TX (US); Kevin Aroom, Houston, TX (US); Charles Cox, Jr., Bellaire, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 923 days.

(21) Appl. No.: 16/076,605

(22) PCT Filed: Feb. 8, 2017

(86) PCT No.: PCT/US2017/017030
§ 371 (c)(1),
(2) Date: Aug. 8, 2018

(87) PCT Pub. No.: WO2017/139384
PCT Pub. Date: Aug. 17, 2017

(65) Prior Publication Data
US 2021/0190758 A1    Jun. 24, 2021

Related U.S. Application Data

(60) Provisional application No. 62/293,120, filed on Feb. 9, 2016.

(51) Int. Cl.
*G01N 33/49* (2006.01)
(52) U.S. Cl.
CPC ................. *G01N 33/4905* (2013.01)
(58) Field of Classification Search
CPC .................................................. G01N 33/4905
See application file for complete search history.

(56) References Cited

U.S. PATENT DOCUMENTS

| | | | | |
|---|---|---|---|---|
| 4,986,964 A | * | 1/1991 | Carr, Jr. | ............. G01N 33/4905 |
| | | | | 73/64.41 |
| 7,192,726 B1 | * | 3/2007 | Carr, Jr. | ................. G01N 33/86 |
| | | | | 435/13 |

(Continued)

FOREIGN PATENT DOCUMENTS

| WO | WO-2008099179 A2 | * | 8/2008 | ............. G01N 11/08 |
|---|---|---|---|---|
| WO | WO-2016205243 A1 | * | 12/2016 | ............... B81B 7/02 |

OTHER PUBLICATIONS

L. Que, M.-H. Li, L.L. Chu, Y.B. Gianchandani: A micromachined strain sensor with differential capacitive readout. (Year: 1999).*

(Continued)

*Primary Examiner* — Farhana A Hoque
*Assistant Examiner* — Joseph O Nyamogo
(74) *Attorney, Agent, or Firm* — Parker Highlander PLLC

(57) ABSTRACT

An apparatus and method for measuring clotting capacity of a patient's blood comprises a probe having a wetted portion, a well to receive a blood sample to contact the wetted portion, a spring element intermediate the wetted portion and a probe support, and a sensor to determine the displacement of the wetted portion resulting from a displacing force imparted to the wetted portion by a clotting blood sample in the well. Embodiments of the apparatus of the present invention may include a variable capacitance displacement sensor, an eddy current variance sensor, a microelectromechanical sensor and an optical instrument. Embodiments of the apparatus may include a current source. The present invention enables reliable detection of mitochondrial dysfunction and sepsis in a blood sample. Embodiments of the apparatus of the invention may be portable. A probe used in such embodiments may be disposable.

9 Claims, 21 Drawing Sheets

(56) References Cited

U.S. PATENT DOCUMENTS

| | | | | |
|---|---|---|---|---|
| 8,789,425 B2* | 7/2014 | Oh | ............... | G01L 1/005 |
| | | | | 73/774 |
| 9,723,996 B2* | 8/2017 | Walker | ............... | A61B 8/08 |
| 9,753,024 B2* | 9/2017 | Gill | ............... | G01N 33/4905 |
| 2002/0168294 A1* | 11/2002 | Carr, Jr. | ............... | G01N 33/4905 |
| | | | | 422/73 |

OTHER PUBLICATIONS

Paul Harrison: Platelet function analysis (Year: 2005).*

* cited by examiner

BLOOD COAGULOMETER AND METHOD

STATEMENT OF RELATED APPLICATIONS

This application depends from and claims priority to PCT/US2017/017030 entitled Blood Coagulometer and Method filed on Feb. 8, 2017, which depends from and claims priority to U.S. Provisional Application No. 62/293,120 filed on Feb. 9, 2016.

FIELD OF THE INVENTION

This application relates to an apparatus and a method of testing a blood sample. More specifically, this application relates to an apparatus and a method for determining the clotting capacity of a sample of blood obtained from a patient. This application further relates to an apparatus and a method for determining the capacity of a clotting blood sample to adhere to a contacted structure, and for reliably diagnosing certain blood conditions.

BACKGROUND OF THE INVENTION

The process of blood coagulation (thrombogenesis) results in blood clotting and involves a coagulation cascade affected by factors including enzymes which cleave downstream proteins. The maintenance of proper clotting balance is critical. Disorders effecting coagulation of a patient's blood can lead to uncontrolled bleeding (hemorrhage) or uncontrolled clotting (thrombosis) that can prevent blood flow to critical organs such as, for example, the heart or the brain. Coagulation may be altered for therapeutic purposes, for example when cardiac stent patients are treated with aspirin.

Tests are available for evaluating the function of the clotting system in the blood of mammals. Commonly used tests confirm functioning of various parts of the enzyme cleavage process, such as prothrombin time (PT) and partial thromboplastin time. An alternative method of testing the clotting system is thromboelastography ("TEG"), described by Trapani, L., in "Thromboelastography: Current Applications, Future Directions," *Open Journal of Anesthesiology*, January 2013. TEG methods include the rotation of a blood sample in a cuvette about a thin wire wetted portion, or probe, to measure clot formation, clot strength and other parameters. The resistance to rotation of the cuvette about the probe is measured to detect blood clot formation.

In addition to the clotting enzyme cascade, which produces fibrin, coagulation is affected by platelet function. Platelet functions include signal transduction, surface adhesion and clot contraction. It is necessary for the blood clot to adhere to surface of the vessel wall in order to slow and to ultimately stop bleeding. Contraction of the clot increases its density, allowing it to oppose the flow of blood.

It is desirable to measure the surface adhesion and contractile functions of blood in order to distinguish normal hemostasis from disease states, and the identification such disorders allow for the proper application of therapy.

SUMMARY OF THE PRESENT INVENTION

Figure 1:
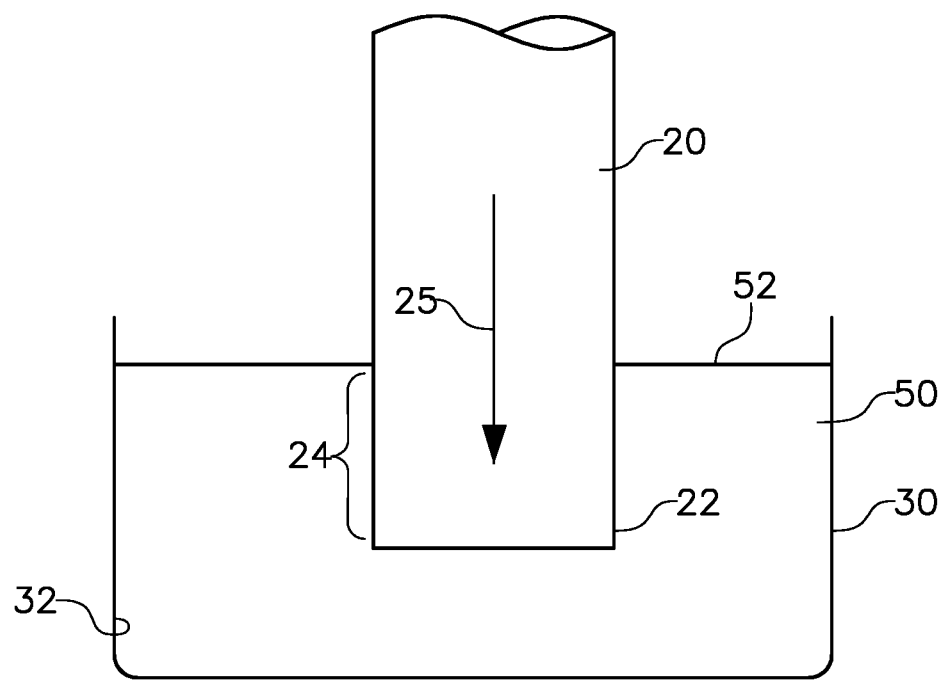
FIG. 1 is an illustration of a downwardly directed displacing force applied by a clotting blood sample to a wetted portion of a probe in passive contact with the clotting blood sample.

Some embodiments of the present invention relate to an apparatus to measure clotting in a blood sample comprising a well to receive a sample of the blood, a probe connected at a support arm at the first end of the probe to a probe support secured in a position relative to the well and having a second end with a wetted portion to be contacted by the blood sample to be tested. The probe support supports the wetted portion of the probe at least partially within the well to contact the blood sample received into the well for testing.

A blood sample introduced into the well contacts the wetted portion of the probe. The probe is passive; that is, the probe is not driven to rotate, reciprocate or oscillate relative to the well, and the well in which the blood sample is introduced for testing does not rotate, reciprocate or oscillate relative to the probe. A blood clot forms within the stagnant blood sample introduced into the well, and the clotting blood sample adheres to the contacted wetted portion of the probe and it contracts as it clots. The adherence of the blood clot to the wetted portion of the probe contacted by the blood sample is attributable to fibrins forming in the clotting blood sample, and contraction of the blood clot is driven by platelets present in the clotting blood sample. As a result of the clotting of the blood sample, fibrins adhere to an interior surface of the well and to the exterior surface of the wetted portion of the probe that is contacted by the blood sample. As platelets contract, the contracting platelets pull the fibrins to apply a downwardly directed displacing force to the wetted portion of the probe. That downwardly directed force is conveyed through the probe to a probe support. It will be understood that there must be an equal and opposite upwardly directed force applied to the probe to balance the downwardly directed displacing force applied to the wetted portion of the probe by the clotting blood sample. As a result of the application of the displacing force imparted to the wetted portion of the probe, the wetted portion of the probe is displaced downwardly within the well relative to the probe support. The magnitude of the displacement of the wetted portion of the probe can be detected optically, visually and/or electronically and it may be observed, measured and/or correlated to the capacity of the blood sample introduced into the well to clot.

It will be understood that preferred embodiments of the present invention include a plurality of electronic devices for measuring the magnitude of displacement of the wetted portion of the probe resulting from the downward force applied by the clotting blood sample. Certain electronic devices included in these preferred embodiments of the apparatus and method of the present invention provide improved sensitivity and accuracy and enable favorable miniaturization of embodiments of the apparatus. While optical displacement sensors, variable capacitance displacement sensors, microelectromechanical device type displacement sensors and varying eddy current displacement sensors are discussed herein below in connection with embodiments of the apparatus and method of the present invention, it will be understood that other electronic devices may be used to detect and/or to measure the displacement of the wetted portion of the probe resulting from contact with a clotting blood sample.

In one embodiment of an apparatus and method of the present invention, one or more spring elements are disposed intermediate the wetted portion of the probe and a probe support. A spring element used in an embodiment of the apparatus or method of the present invention elastically deforms according to a spring constant in response to the downwardly directed displacing force applied to the wetted portion of the probe by the clotting blood sample. In some embodiments of the apparatus of the present invention, a plurality of spring elements are disposed intermediate the wetted portion of the probe and the probe support. The plurality of spring elements may together elastically deform according to their collective spring constants in response to a downwardly directed displacing force applied to the wetted portion of the probe by a clotting blood sample. Spring elements that can be disposed intermediate the wetted portion of the probe and the probe support in embodiments of apparatus of the present invention include, but are not limited to, coil springs, which may be referred to as helical springs, beam springs, cantilevered springs and folded cantilever springs, and springs may be integral with the probe, such as cantilevered spring elements. It will be understood that an alternative spring element can also use a captured volume of gas to temporarily store energy while presenting a predictable and determinable resistance to displacement of the wetted portion of the probe. A spring element, as that term is used herein, includes all mechanical devices for storing energy and producing some associated amount of elastic deformation as a result of the storing of energy within the spring element.

Embodiments of an apparatus and method of the present invention may include the use of devices used for measuring the displacement of the wetted portion of the probe as a result of the downwardly directed displacing force applied to the wetted portion by a clotting blood sample. In one basic embodiment of an apparatus and method of the present invention, an optical instrument displacement sensor is disposed laterally to the probe. A light source such as, for example, but not by way of limitation, a light emitting diode (LED), may be provided to enable the optical instrument displacement sensor to be used for observing and measuring the deflection and/or the displacement of the wetted portion of the probe relative to a fixed object such as, for example, the probe support or the well. The deflection of the spring element relative to the probe support can be measured and correlated to a displacing force imparted to the wetted portion of the probe by the clotting action of the blood sample. In another embodiment of the apparatus of the present invention, an optical instrument may be used along with a laser light source to impinge on a portion of the probe both before and after the application of the displacing force by the clotting blood sample. In another basic embodiment of the apparatus of the present invention, an optical instrument and a laser light source may be used along with one or more mirrors to reflect and redirect the laser light from the laser light source to magnify the displacement of the probe to enable improved measurement accuracy.

One embodiment of the apparatus and method of the present invention comprises a well to receive the blood sample, a probe support secured in a position relative to the well, a spring element coupled intermediate the probe support and a wetted portion of the probe supported within the well, and an optical instrument displacement sensor disposed laterally to at least one of the wetted portion of the probe and the spring element, wherein the introduction of a volume of a blood sample into the well wets the exterior surface of the wetted portion of the probe and wherein the clotting within the blood sample imparts a downwardly directed displacing force to the wetted portion of the probe that results in a displacement of the wetted portion of the probe relative to the probe support resulting in deformation of the spring element. The displacement of the wetted portion of the probe is measured using the optical instrument displacement sensor, and the measured displacement is correlated to the capacity of the blood sample to clot.

One embodiment of the apparatus and method of the present invention further includes a well having an interior surface that is treated and/or conditioned to one of promote and impair the adherence of the clotting blood sample to the interior surface of the well as it clots. For example, but not by way of limitation, an embodiment of the apparatus and method of the present invention may include a wetted portion of the probe having an interior surface that is manufactured, shaped, treated and/or conditioned to promote adherence of the blood sample to the wetted portion of the probe as it clots. As a further example, an embodiment of the apparatus and method of the present invention includes an interior surface of the well that provides a surface with undulations and/or roughness to promote adherence of the clotting blood sample to the well. As a result of the roughened or undulating surface on the interior of the well, the clotting blood sample may remain in adherence with the well and the displacing force applied to the wetted portion of the probe by the clotting sample of blood may be maximized.

Another embodiment of the apparatus and the method of the present invention includes a well having an interior surface that is treated and/or conditioned to limit the adherence of the clotting blood sample to the interior surface of the well as it clots. For example, an embodiment of the apparatus and method of the present invention may include an interior surface of the well that is manufactured, treated and/or conditioned to provide an exceedingly smooth surface to which the clotting blood sample deposited into the well can adhere. As a result of the smooth surface on the interior of the well, the clotting blood sample may adhere to both the wetted portion of the probe and the interior surface of the well, and the clotting blood sample may become detached from the interior surface of the well at a point at which the capacity of the clotting blood sample to adhere to the smooth interior surface of the well is overcome by the contractile forces acting between the blood clot and the wetted portion of the probe. These contractile forces may, if sufficient, suddenly displace the blood clot from the adhered position with the smooth interior surface of the well and towards the wetted portion of the probe that is contacted by the clotting blood sample. It will be understood that the measure of the force and/or displacement at which the blood clot detaches from the smooth interior surface of the well can be measured and correlated to provide indications of the capacity of the blood sample to adhere during clotting to a surface having a known roughness. This embodiment of the apparatus and method of the present invention can be especially useful for testing the capacity of fibrinogens in the blood to adhere to structures during the clotting process.

It will be understood that the interior surface of the well, like the exterior surface of the wetted portion of the probe, in embodiments of the apparatus and method of the present invention, may be manufactured, treated or conditioned to enhance the suitability of the well and the wetted portion of the probe for the type and mode of the testing being performed on a blood sample, and that these components may be adapted to together enable testing of the capacity of a blood clot to generate and impart a maximum displacing force (e.g., conditioning the exterior surface of the probe and/or the interior surface of the well to promote adherence of a clotting blood sample) or to measure the capacity of a blood clot to adhere to a structure (e.g., conditioning the exterior surface of the probe and/or the interior surface of the well to promote a sudden failure of adherence and release of the component from the clotting blood sample).

One embodiment of the apparatus of the present invention includes a probe having a radially enlarged wetted portion to enhance the downwardly directed displacing force that is imparted to the wetted portion of the probe by the clotting blood sample. One embodiment of the apparatus of the present invention includes a wetted portion of a probe having a radially enlarged portion that is one of bulbous, disc-shaped (plate-shaped), rounded and frusto-conical in shape.

One embodiment of the apparatus of the present invention includes a spring element that is integral with the probe. A probe may include a wire portion as a support arm that extends from a probe support in a cantilevered mode. In this embodiment, the wire portion, which may be referred to as a support arm, is deflected in a cantilever mode by the downwardly directed displacing force applied by the clotting blood sample to the wetted portion of the probe. One embodiment of the apparatus of the present invention includes a probe support having a wire portion or support arm extending from the probe support in a cantilevered mode to a non-linear or angled portion of the probe that is positioned over the well into which the blood sample is introduced. The non-linear or angled portion is intermediate the wetted portion of the probe and the probe support. The wire portion or support arm, which acts as an integral spring element, is deformed in a cantilever mode according to the magnitude of the displacing force applied to the wetted portion of the probe by the clotting blood sample introduced into the well.

One embodiment of the apparatus of the present invention includes a probe support having a more rigid wire portion or support arm with a pivoting member such as, for example, a hinge disposed intermediate the wire portion or support arm and the wetted portion of the probe. This rigid wire portion or support arm is not integral with the spring element as is the support arm that can be deflected from its original shape by application of force to the wetted portion of the probe, and the apparatus may include an external spring element disposed intermediate the probe and the probe support.

One embodiment of the apparatus of the present invention includes a well that is disposed on or within a tray or base that is connected to the probe support. The tray or base can support other components of the apparatus, and the tray or base can include a well that is integral to the tray for receiving an introduced blood sample. Other embodiments of the apparatus of the present invention may include a well having a plurality of inserts having differing interior surface roughness, differing interior surfaces or surface treatments or differing surface agents applied thereto for conditioning the well.

One embodiment of the apparatus of the present invention includes a probe support having a resiliently flexible support arm with a stationary first end coupled or connected to the probe support and a movable second end extending over the well to support the wetted portion of the probe within the interior of the well. The flexible support arm, which is preferably a wire portion, is itself a spring element (integral spring element) so that the application of a displacing force to the wetted portion of the probe by the clotting blood sample in the well deflects at least a portion of the support arm from an original position and shape to a deflected position and an elastically deformed shape. One embodiment of the apparatus of the present invention includes a wetted portion of the probe that is pivotally coupled to a support arm of a probe support that is made of a wire portion having a known spring constant. One embodiment of the apparatus of the present invention includes a wetted portion of the probe supported by a spring element to resist downward displacement of a wetted portion of the probe resulting from the application of a displacing force by the contraction of a clotting blood sample introduced into the well.

The present invention further comprises a method of measuring the capacity of the blood to clot. One embodiment of the method of the present invention comprises providing a well to receive the blood sample, providing a probe support in a fixed position relative to the well, providing a probe having a wetted portion with an exterior surface supported from the probe support with the wetted portion at least partially within the well, disposing a spring element one of intermediate the probe and the probe support and integral with the probe, coupling the probe to one of the spring element and the probe support to support the wetted portion of the probe at least partially within the well, disposing a displacement sensor, such as, for example, an optical instrument laterally to one of the spring element and the probe, introducing a volume of a blood sample into the well to wet the exterior surface of the wetted portion of the probe, and using the optical instrument to measure the displacement of the probe resulting from the application of a displacing force to the wetted portion of the probe and resulting from the contraction of the clotting blood sample, wherein the measured displacement of the probe indicates the capacity of the blood sample to clot. Alternately, the displacement sensor may be a microelectromechanical device displacement sensor that engages a portion of the probe, measures the displacement of the portion of the probe and produces a signal corresponding to the sensed displacement.

Embodiments of the apparatus and method of the present invention provide for the reliable and accurate measurement of platelet activity in the blood. The capacity to measure platelet activity provides clinically significant implications for patients with conditions causing dysfunctional coagulation of the blood. For example, but not by way of limitation, the capacity to measure platelet activity can be used to guide blood product administration in a hemorrhaging patient, to inform the pharmacologic plan for the patient with coronary artery disease or to characterize the effect of clinically relevant anti-platelet drugs like, for example, aspirin, and can define an individual patient's response to these drugs or the status of the patient's recovery when these drugs are withheld. Embodiments of the apparatus and method of the present invention enable the measurement and characterization of energy conversion within and forces generated by platelets during the blood clotting process.

Embodiments of the apparatus and method of the present invention have also been used to confirm basic properties known to be associated with blood coagulation. Platelet energetics offer unique biologic signals that have in the past proven to be difficult to measure. These unique biologic signals can be identified, characterized and accurately measured using embodiments of the apparatus and method of the present invention, and this information can be used to reliably identify compounds or therapies that either accelerate or inhibit platelet metabolism, fostering a much better understanding of measured energetic signals such as, for example, platelet respiration and oxygen consumption. This information is easily translatable to characterize the systemic physiology of a patient and it is a reliable indicator of systemic mitochondrial health and platelet energetics.

Embodiments of the apparatus and method of the present invention may also be used to provide for early diagnosis of the development of, among other conditions, sepsis in a patient. More specifically, embodiments of the apparatus and method of the present invention may be used to detect a reduction in the energy conversion in, and the resulting contraction forces developed during, coagulation of a blood sample obtained from a patient of interest.

Other embodiments of the apparatus and method of the present invention provide for the diagnosis of sepsis in a patient. For example, but not by way of limitation, an embodiment of the method of the present invention comprises the steps of: 1) obtaining a blood sample from a patient; 2) using an embodiment of one of the apparatus and method of the present invention for measuring forces generated within a clotting blood sample taken from the patient; 3) comparing the measured forces detected within the blood sample to the measured forces detected within one of a blood sample previously obtained from the patient and a blood sample obtained from a different patient known to be free of sepsis or other mitochondrial dysfunction that affects clotting; and 4) detecting a reduced capacity of the blood sample to generate forces during contraction resulting from blood coagulation. If the detected reduced capacity of the blood sample to generate forces during contraction resulting from blood coagulation indicates a sufficient reduction in the amount of force developed within the blood sample taken from the patient of interest during contraction resulting from coagulation of the blood sample, the patient can be diagnosed with sepsis.

Still other embodiments of the apparatus and method of the present invention provide for the diagnosis of sepsis, a mitochondrial dysfunction or a mitochondrial disorder in a patient of interest. For example, but not by way of limitation, an embodiment of a method of the present invention comprises the steps of: 1) obtaining a blood sample from a patient; 2) using an embodiment of one of the apparatus and method of the present invention for measuring forces generated within the clotting blood sample taken from the patient; 3) comparing the measured forces detected within the blood sample to the measured forces detected within one of a blood sample previously obtained from the patient and a blood sample obtained from a different patient known to be free of mitochondrial dysfunction and sepsis; and 4) detecting a reduction in the force developed during contraction resulting from coagulation of the blood sample obtained from the patient as compared to the force developed during coagulation of one of a previously obtained blood sample from the patient and a blood sample obtained from a person known to be free of sepsis and mitochondrial dysfunction disorders. Mitochondrial dysfunction disorders that can be detected using embodiments of the method include, but are not limited to, cancer, neurodegeneration, diabetes and ischemia/reperfusion injury such as those resulting from, for example, myocardial infarction and stroke, acute inflammatory conditions, chronic inflammatory conditions, cardiogenic shock, Alzheimer's disease, Huntington's disease, schizophrenia, migraine headaches, Parkinson's disease and Down syndrome.

The ease of obtaining a small volume of a patient's blood, combined with the small amount of time needed to use an embodiment of an apparatus or method of the present invention, allows a medical practitioner to obtain multiple blood samples over a recorded time period and to detect, monitor and quantify the development of a pre-shock septic condition. Additionally, these factors enable a medical practitioner to use an embodiment of an apparatus or method of the present invention to detect, monitor and quantify patient improvement as a detected and treated condition or disorder resolves for conditions that are not chronic, such as, for example, but not limited to, sepsis.

While not limited by a particular mechanism, embodiment of the apparatus and method of the present invention enable the determination of the total energy produced by platelets during coagulation of a blood sample as indicated by the integral of the force waveform resulting from platelet contractile force. More specifically, the determination of the area under a force curve represents the amount of mechanical work done by and energy produced by the coagulating blood sample. The principle of work-energy equivalence applies to this system as it does to the mechanical equivalent in the more familiar and well-known mechanical work imparted to or by a spring element and as it does to the chemical equivalent of chemical energy (adenosine triphosphate or "ATP"). Mechanical work can be used to store energy within a spring element by energizing the spring element from a relaxed mode to an energized mode or compressed mode. In this energy conversion, work is converted to potential energy, which is stored in the spring element resulting in an increase in the energy within the spring element. The amount of work imparted to the spring element, and the resulting potential energy stored in the spring element, can be quantified by determination of the integral of the equation that relates applied force to displacement of the spring element. In the chemical equivalent, the formation of ATP is the result of the increase in energy in the system resulting from platelet production of ATP.

Returning to the mechanical spring equivalent, it is known that the work imparted to a spring element displaced from a relaxed mode to a deflected, compressed or energized mode, where the spring element has a linear spring constant, can be determined as the integral of the equation representing the work imparted to the spring element. For a spring constant of k, in units of Newtons per meter (N/m), the amount of work imparted to a spring element displaced from a relaxed mode to a deflected, compressed or energized mode is analogous to the amount of work yielded by platelets resulting from coagulation of a clotting blood sample. The amount of work stored in a spring element, yielded by a spring element, or yielded by the chemical equivalent of a clotting blood sample, can be determined in terms of the amount of the measured displacement x as:

$$W=\int_0^t F \cdot v \, dt = \int_0^t kx v_x \, dt = \tfrac{1}{2}kx^2.$$

It will be understood that, in the context of embodiments of the apparatus or method of the present invention, the displacement is the measured movement of a wetted portion of a probe contacted by the clotting blood sample. Integration of the force applied to the wetted portion of the probe by the clotting blood sample directly over time can be done using numerical methods. The spring constant k is dependent on the dimensions of one or more spring elements, such as spring beams in the beam spring, and is known. This integral expresses the amount of energy produced by a given blood sample during the contraction phase of blood clotting and, when normalized by the platelet count, yields information about the global capacity of the patient to utilize energy substrates. Thus, the described highly sensitive embodiments of the apparatus and methods that measure platelet contractile force can also be used to identify mitochondrial dysfunction or sepsis at an early stage. This can be particularly valuable in early detection of sepsis and a pre-shock condition.

Sepsis is a condition of the blood that is currently difficult to diagnose before end organ dysfunction is imminent. Sepsis is a health condition that is common, costly to treat and often deadly. Hospitals and medical practitioners often use algorithms to detect potential cases of sepsis and treatment protocol often requires physicians to document patient responses. These algorithms are typically based on the patient's observed temperature, blood pressure, heart rate and respiratory rate. In particular, a patient's respiratory rate is a major determinant of the sepsis state and an observable condition that is often poorly documented by medical practitioners and in most hospitals. As a result, what are often considered to be available observable early indications of sepsis generate many false positives, while more specific indications all provide a very late signal which may be learned after the onset of organ dysfunction within the patient. Embodiments of the apparatus and method of the present invention enable a medical practitioner or hospital to obtain a patient's blood sample and to quickly and inexpensively test the blood sample to detect the onset of sepsis, thereby enabling early diagnosis and treatment of a condition that kills at least 500,000 people or more each year.

The capacity of embodiments of the apparatus and method of the present invention to detect and measure platelet contractile force in a patient's blood sample as an indicator of mitochondrial dysfunction has been confirmed through tests in which platelets were exposed to differing concentrations of inhibitors such as, for example, sodium azide which leads to mitochondrial dysfunction as described in more detail below.

Among other advantages, the ease of obtaining a small volume of patient blood in combination with the capacity for rapid use of the of embodiments of the apparatus and method of the present invention enables a medical practitioner or hospital to obtain multiple samples over time, to test the samples, and to thereby monitor the development of a pre-shock septic condition or to monitor patient improvement as the non-chronic disorder such as, but not limited to, sepsis, resolves.

The determination of platelet energetics and mechanics provides unique biologic signals requiring distinct devices for measurement. Experiments have proven methods to accelerate or inhibit platelet metabolism, thereby fostering an understanding of measured energetic signals like platelet respiration and oxygen consumption as indicators of systemic physiology of a patient and biomarkers of systemic mitochondrial health including, but not limited to, sepsis patients, hypocoagulable patients and hypercoagulable patients in the hospital and anticoagulated patient at home. However, platelet energetics have proven difficult to measure. Platelet mechanics such as platelet contraction force, contraction rate or clot elastic modulus are readily captured using the device. Platelet dysfunction is often categorized into disease causing metabolic derangements like sepsis or disease causing mechanical dysfunction like von Willebrand disease.

Platelet energetics governs global platelet function and the balance of metabolic supply and demand. All biologic processes occurring after platelet activation are energy dependent, susceptible to disorders of mitochondrial function or glycolysis. Changes in energetic processes like mitochondrial function affect an array of measurable signals. For example, sodium azide inhibits the energetic process of oxidative phosphorylation by inhibiting complex IV in the electron transport chain, causing a dose dependent decrease in measured platelet respiration. This mode of inhibition parallels that associated with Alzheimer's disease where levels of complex IV in the platelet mitochondria are significantly reduced (see, for example, *Platelet Energetics and Mechanics: A Review* by M. J. George, C. E. Wade, C. S. Cox and B. S. Gill).

DETAILED DESCRIPTION OF PREFERRED EMBODIMENTS

Embodiments of the apparatus of the present invention can be used to determine the clotting capacity of a sample of blood, and embodiments of a method of the present invention can be used to determine the capacity of a sample of blood to coagulate or clot.

Mammal blood clots by forming a network of polymerized fibrins. A circulating monomer called fibrinogen is induced to polymerize into fibrin, which forms the physical clot. Fibrins bind one to the others and form a network of fibrins, or a fibrin skeleton. Increasing fibrin polymerization results in a change in the viscosity of a clotting blood sample and, with increasing fibrin network binding, the clot begins to behave as a solid composite as opposed to behaving as a fluid. The fibrins adhere to the surfaces of structures contacted by the blood sample as it clots. The adherence of the fibrins binds the fibrin skeleton to the structure and, as the clotting progresses and the fibrin skeleton contracts. As a result of the contracting of the fibrin skeleton and adherence of fibrins to contacted structures, a displacing force may be applied to a structure to which the fibrins have adhered. A displacing force resulting from fibrin adherence to the structure can be measured and correlated to the capacity of the blood sample to clot.

Embodiments of the apparatus and the method of the present invention provide reliable, repeatable tests of platelet function by measuring the amount of force developed during contraction of a sample of blood during coagulation, thereby yielding a distinct clinical signal in response at varying levels of platelet function as induced by platelet number, the presence of antiplatelet drugs, or an individual patient's phenotypic variation in platelet function.

Although other "platelet assays" have been developed, most have limited clinical application. One reason for this results from attempting to substitute an easily measured quantity as a proxy for overall platelet function. Traditionally, bleeding time is the test done to assess platelet function. The patient is made to bleed and the time it takes to stop bleeding is considered to be an indicator of platelet function. There are currently available several point-of-care platelet assays such as, for example, Plateletworks® (Helena Labs, Beaumont, Texas, U.S.A.) which utilizes cell count after activation, PFA-100/200 (Siemens) which measures the ability of citrated patient blood to close off a fixed opening in a membrane, and VerifyNow® (Accriva Diagnostics) a platelet aggregometer that utilizes changes in optical density that result from the clumping of platelets in a blood sample. However, all of these assays have limitations.

There are also assays that are targeted at specific proteins or portions of the clotting process such as, for example, Gp IIb/IIIa receptor binding, but no single step gives a clear indication of the complex, time-evolving process of clot formation.

In contrast to these available tests, embodiments of the apparatus and methods of the present invention provide a means of obtaining a detailed representation of platelet function throughout the activation and contraction phases of platelet function. These apparatus and methods are amenable to activation of the clotting process using pharmacological agents to obtain a more rapid result, or can proceed more slowly using only surface activation to initiate clotting to explore the relative effects of adhesion on overall clot function. The extreme sensitivity of the apparatus and methods provided herein allow the detection of small differences in function that are not discernible by currently available tests.

This innovative approach improves upon existing platelet assays because it allows the clot to behave in a physiologically relevant way, and the measurement probe and spring allow the actin/myosin machinery to contract through a relatively long linear distance. All three facets of platelet function (adhesion, contraction, signal transduction) contribute to the eventual result, which provides a time-based profile of force generated with very high sensitivity (that is, sub-micronewton sensitivity).

There are multiple disorders (such as, but not limited to, uremia, Glanzmann's thrombasthenia, and others) where platelet counts may be normal but function is clearly impaired as demonstrated by clinically important bleeding. Even a population of otherwise normal individuals will demonstrate a range of response to a given antiplatelet drug; this has been most clearly demonstrated for clopidogrel (Plavix®). These methods also facilitate the transfusion of platelets for the prevention of bleeding complications in thrombocytopenia. Transfusion guidelines utilize a variety of threshold values to trigger platelet transfusion; however, clinicians routinely see patients with values lower than the thresholds for whom no bleeding occurs. This is a clear example of how variable platelet function overrides the simple platelet count in generating clinically important bleeding behavior. These methods allow clinicians to evaluate platelet function as well as count and allow better targeting of expensive platelet transfusions, such as those used routinely in, among others, oncology, neonatology, and trauma resuscitation.

FIG. 1 is an illustration of a downwardly directed displacing force applied as indicated by the arrow 25 by contraction of a clotting blood sample 50 to a wetted portion 24 of a probe 20 that is contacted by the blood sample 50. The wetted portion 24 of the probe 20 may be positioned within the well 30 and the blood sample 50 may be introduced into the well 30 to contact the wetted portion 24 of the probe 20 for testing the capacity of the blood sample 50 to clot, or the blood sample 50 may be introduced into the well 30 and the probe 20 then introduced into the blood sample 50 to wet the wetted portion 24 of the probe 20 to begin the test. The extent of the wetted portion 24 of the probe 20 depends on the volume of the blood sample 50 and the level of the blood interface 52. Fibrins that form in the blood sample 50 adhere to the interior surface 32 of the well 30 and to the exterior surface 22 of the wetted portion 24 of the probe 20 as the platelets of the blood sample 50 contract during clotting of the blood sample 50. The adherence of the fibrins to the interior surface 32 of the well 30 and to the wetted portion 24 of the probe 20, and the contraction of the platelets of the blood sample 50, result in a downwardly directed displacing force as illustrated by the arrow 25 applied to the probe 20. This interaction between the clotting blood sample 50 and both of the interior surface 32 of the well 30 and the wetted portion 24 of the probe 20 causes the displacing force applied to the probe 20. The observation of the displacement of the probe 20 in response to the applied displacing force and the measurement of the displacement enable the determination of the capacity of the blood sample 50 to clot.

Figure 2:
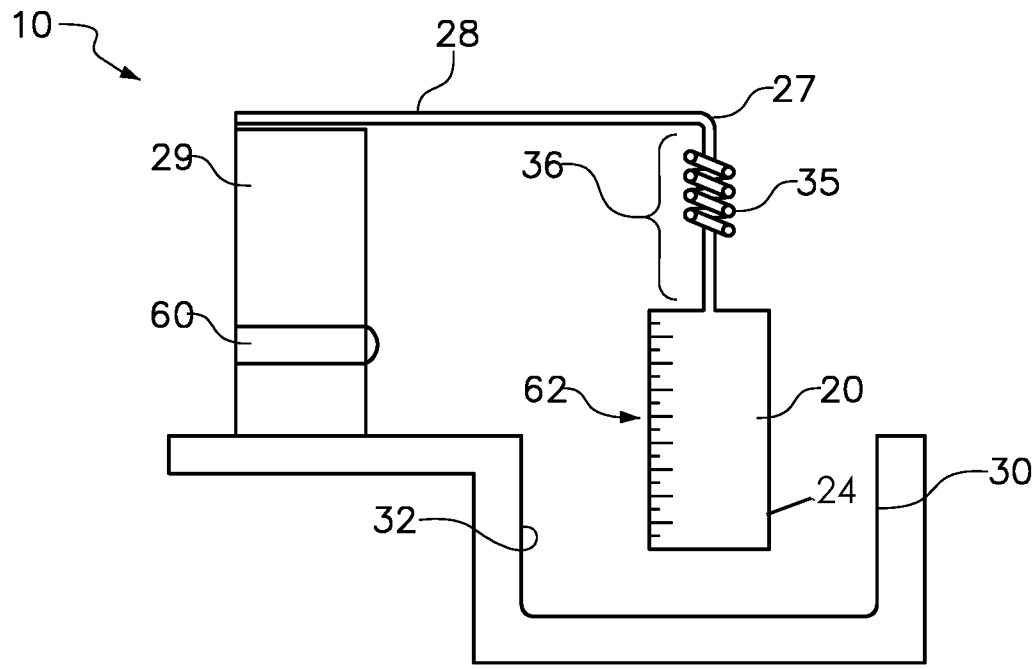
FIG. 2 is an illustration of an embodiment of an apparatus of the present invention for determining the capacity of a blood sample to clot.

FIG. 2 is an illustration of an embodiment of an apparatus 10 of the present invention for determining the capacity of a blood sample 50 to clot. The apparatus 10 utilizes the interaction between a clotting blood sample 50 (not shown in FIG. 2) received into a well 30 and a probe 20 having a wetted portion 24 suspended in the well 30 and contacted by a blood sample 50 as illustrated in FIG. 1. The apparatus 10 of FIG. 2 comprises a well 30 having an interior surface 32, a probe support 29 that is fixed relative to the well 30, a probe 20 supported from the probe support 29 with at least some of a wetted portion 24 of the probe 20 suspended within the well 30. The embodiment of the apparatus 10 of the present invention illustrated in FIG. 2 further comprises a spring element 35 disposed intermediate the probe support 29 and the wetted portion of the probe 20, an optical instrument 60 displacement sensor disposed laterally to the probe 20 and gradations 62 disposed on a portion of the probe 20 that can be observed using the optical instrument 60. Optionally, the optical instrument 60 can be supported on the probe support 29 as illustrated in FIGS. 2-7. The probe 20 further includes a support arm 28 to couple with and support a spring element 35 that, in turn, supports the wetted portion 24 of the probe 20 within the well 30. The spring element 35 of FIG. 2 has an original length 36. Optionally, the apparatus 10 may further comprise an angled portion 27 intermediate the wetted portion 24 of the probe 20 and the probe support 29.

Figure 3:
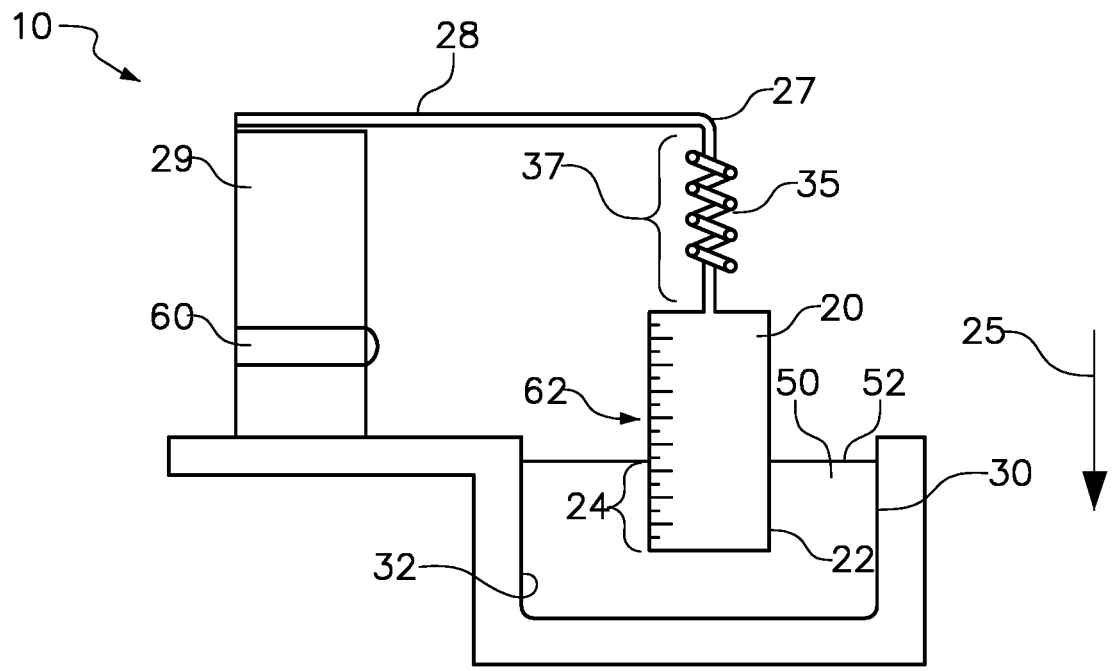
FIG. 3 is the illustration of the apparatus of FIG. 2 after a spring element supporting a wetted portion of a probe of the apparatus is deformed from an original configuration by a downwardly contractile displacing force applied by a blood sample to the wetted portion of the probe.

FIG. 3 is the illustration of the embodiment of the apparatus 10 of the present invention illustrated in FIG. 2 after a blood sample 50 is introduced into the well 30 to contact at least some of the wetted portion 24 of the exterior surface 22 of the probe 20. The spring element 35 of the apparatus 10 disposed below the angled portion 27 is illustrated as being elongated from its original length 36 shown in FIG. 2 to an elastically deformed length 37 due to the application of a downwardly directed displacing force in the direction of arrow 25 by the clotting blood sample 50 to the wetted portion 24 of the probe 20. The blood sample 50 introduced into the well 30 contacts and adheres to the wetted portion 24 of the exterior surface 22 of the probe 20 and adheres to the interior surface 32 of the well 30. As clotting of the blood sample 50 progresses, the adherence of fibrins and the contraction of the clotting blood sample 50 imparts the displacing force drawing the wetted portion 24 of the probe 20 towards the interior 32 of the well 30. The amount of deformation of the spring element 35 from the original length 36 illustrated in FIG. 2 to the deformed length 37 illustrated in FIG. 3 is a function of the magnitude of the displacing force applied to the wetted portion 24 of the probe 20 by the clotting of the blood sample 50 and of the spring constant of the spring element 35. The size, the shape and surface area of the wetted portion 24 of the probe 20 affect the magnitude of the displacing force applied to the wetted portion 24 of the probe 20 by the clotting of the blood sample 50. The optical instrument 60 displacement sensor may be used to determine the displacement of the wetted portion 24 of the probe 20 as a difference between an originally aligned gradation 62 and a gradation 62 that is aligned after downward displacement of the probe 20.

Figure 4:
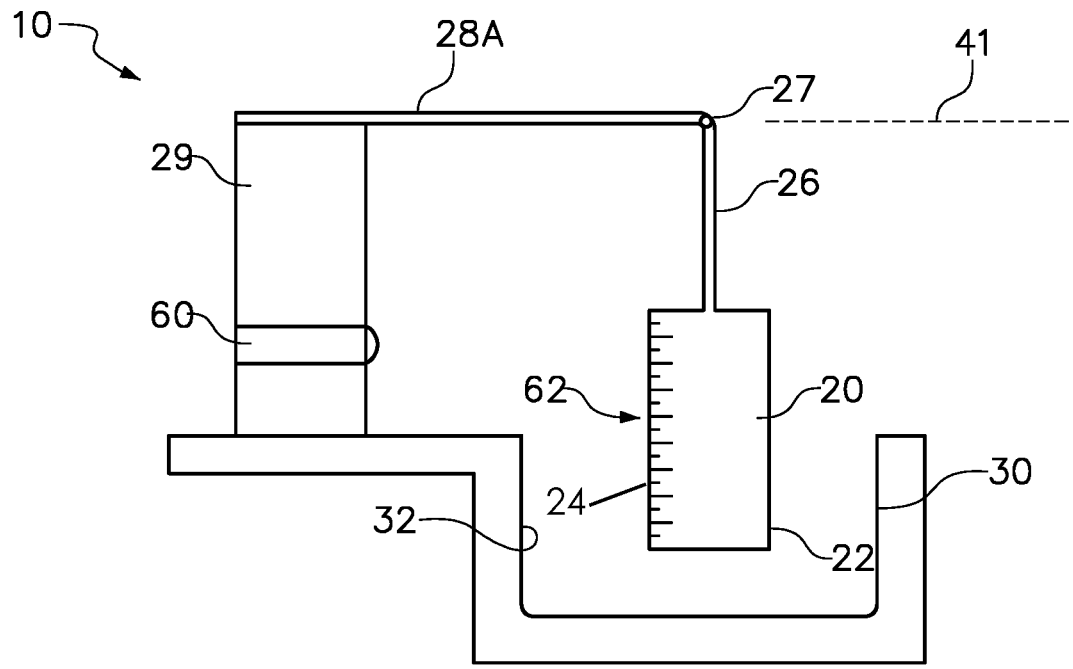
FIG. 4 is an illustration of an alternative embodiment of an apparatus of the present invention for determining the capacity of a blood sample to clot with an integral spring element of the probe disposed in a cantilever mode.

FIG. 4 is an illustration of an alternative embodiment of an apparatus 10 for determining the capacity of a blood sample 50 to clot. FIG. 4 illustrates an apparatus 10 comprising a well 30 having an interior surface 32 and a probe 20 having a flexible support arm 28A connected in a cantilevered mode between a probe support 29 and a support stem 26. An angled portion 27 is disposed within the probe 20 intermediate the support stem 26 and the support arm 28A. Optionally, the angled portion 27 illustrated in FIG. 4 is a pivoting angled portion that accommodates a change in the angle of the angled portion 27 as displacement of the wetted portion 24 of the probe 20 occurs. The probe support 29 is fixed relative to the well 30 and a probe 20 supported from the flexible and cantilevered support arm 28A is suspended within the well 30. The flexible support arm 28A of the probe support 29 supports the probe 20 and, at the same time, functions as an integral spring element disposed intermediate the wetted portion 24 of the probe 20 and the probe support 29 because it may be deflected, in a cantilever mode, from its original position shown in FIG. 4 by a downwardly directed displacing force applied to the wetted portion 24 of the probe 20 by the clotting blood sample 50 (not shown in FIG. 4) introduced into the well 30. An optical instrument 60 is disposed laterally to the wetted portion 24 of the probe 20 and gradations 62 are provided on a portion of the probe 20 that can be observed using the optical instrument 60. It will be noted that the original position of the flexible support arm 28A extending from the probe support 29 is indicated by the dotted line 41.

Figure 5:
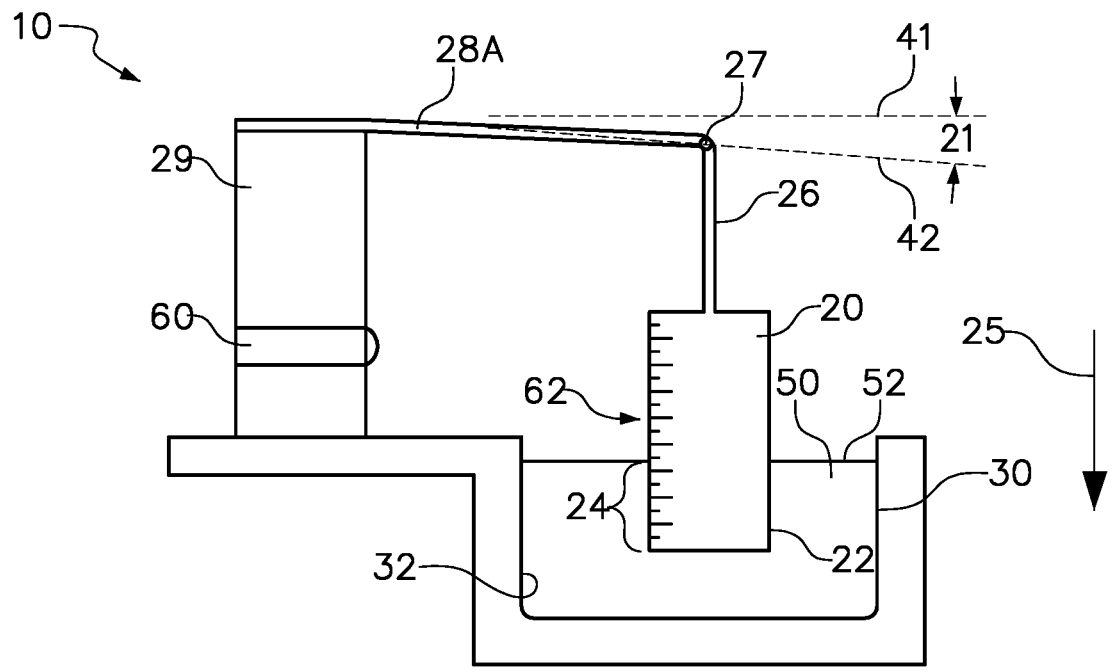
FIG. 5 is the illustration of the apparatus of FIG. 4 after a support arm of the probe supporting the wetted portion of the probe of the apparatus is resiliently deflected downwardly in a cantilever mode from the original undeflected position of FIG. 4 by a downwardly directed contractile displacing force applied by a clotting blood sample to the wetted portion of the probe.

FIG. 5 is the illustration of the apparatus 10 of FIG. 4 after a blood sample 50 is introduced into the well 30 to contact a wetted portion 24 of the exterior surface 22 of the probe 20. The clotting of the blood sample 50 introduced into the well 30 to fill the well 30 up to the blood interface 52 results in a downwardly directed displacing force applied to the probe 20 and to the support stem 26 of the probe 20 in the direction of arrow 25 to cause a downwardly deflection of the support arm 28A through an angle 21. The angle 21, which is the angular difference between the original angular position of the flexible support arm 28A indicated by the dotted line 41 and the deflected position of the support arm 28A indicated by the dotted line 42 can be measured and correlated to the properties of the flexible support arm 28A to determine the magnitude of the displacing force applied to the probe 20 by the clotting blood sample 50. The magnitude of the displacing force can be correlated to the capacity of the blood sample 50 to clot. Alternately, the optical instrument 60 and the gradations 62 on the probe 20 may be used to determine the displacement of the wetted portion 24 of the probe 20 as a difference between an originally aligned gradation 62 and an adjacent gradation that is aligned with the optical instrument 60 after displacement of the probe 20. Optionally, a pivoting angled portion 27 such as, for example, a hinge, may be disposed intermediate the wetted portion 24 of the probe 20 and the support arm 28A to minimize lateral movement of the wetted portion 24 of the probe 20 during deflection of the support arm 28A through the angle 21.

In the alternative embodiment of the apparatus 10 illustrated in FIGS. 4 and 5, the spring element of the apparatus 10 is integral with the support arm 28A of the probe support 29 and the application of a displacing force in the direction of arrow 25 applied to the wetted portion 24 of the probe 20 by the clotting blood sample 50 produces the downwardly directed deflection of the support arm 28A.

Figure 6:
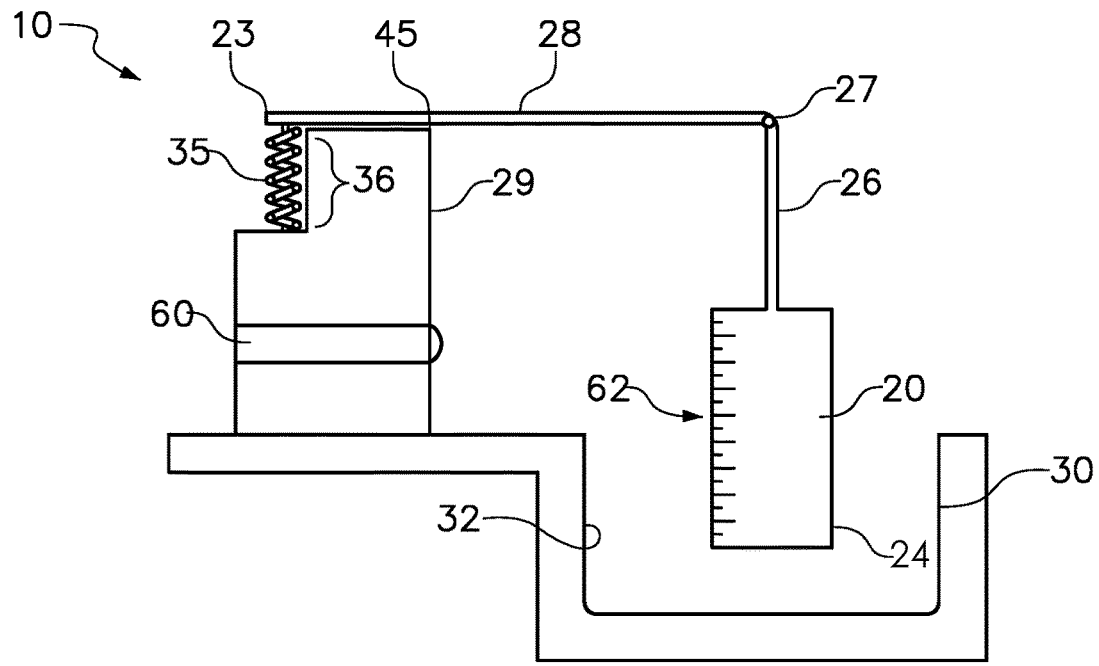
FIG. 6 is an illustration of an alternative embodiment of an apparatus for determining the capacity of a blood sample to clot with an external spring element disposed in an original configuration intermediate the probe and a probe support.

FIG. 6 is an illustration of a second alternative embodiment of an apparatus 10 for determining the capacity of a blood sample 50 to clot. FIG. 6 illustrates an apparatus 10 comprising a well 30 having an interior surface 32, a probe support 29 having a rigid support arm 28 that is fixed relative to the well 30, a probe 20 suspended from the probe support 29 to dispose the wetted portion 24 within the well 30 and an external spring element 35 disposed intermediate the probe support 29 and the probe 20 and, more specifically, intermediate the spring element 35 and an attachment end 23 of the probe 20. A support stem 26 is disposed intermediate the wetted portion 24 of the probe 20 and the rigid support arm 28. An optical instrument 60 is disposed laterally to the probe 20 and gradations 62 disposed on a portion of the probe 20 can be observed using the optical instrument 60. The support arm 28 of the embodiment of the apparatus 10 of FIG. 6 is pivotally coupled to pivot about a portion 45 of the probe support 29 upon deformation of the spring element 35. The spring element 35 has an original length 36 as it supports the wetted portion 24 of the probe 20 within the well 30. Optionally, a pivoting member 27 such as, for example, a hinge, is disposed intermediate the probe support 29 and the wetted portion 24 of the probe 20 to minimize lateral movement of the probe 20 within the well 30.

Figure 7:
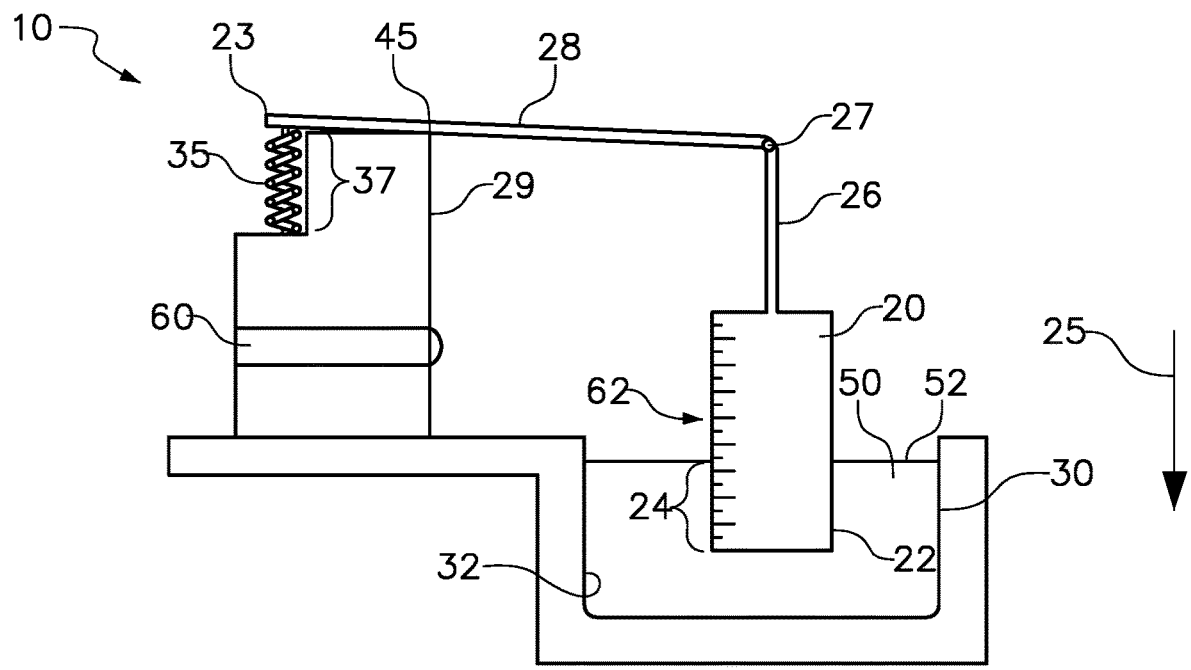
FIG. 7 is the illustration of the apparatus of FIG. 6 after the external spring element supporting a support arm of the probe of the apparatus is elastically deformed from the original configuration by application of a downwardly contractile displacing force applied by a clotting blood sample to the wetted portion of the probe.

FIG. 7 is the illustration of the apparatus 10 of FIG. 6 after a blood sample 50 is introduced into the well 30 up to blood interface 52 to contact a wetted portion 24 of the exterior surface 22 of the probe 20. The contraction of the clotting blood sample 50 and the resulting adherence of the blood sample 50 to the interior surface 32 of the well 30 imparts a downwardly directed displacing force in the direction of arrow 25. The rigid support arm 28 of the probe 20 pivots about the portion 45 of the probe support 29 in response to the displacing force and the spring element 35 of the apparatus 10 deforms from its original length 36 (shown in FIG. 6) to a deformed length 37 due to the application of a displacing force to the wetted portion 24 by the clotting blood sample 50. The deformation of the spring element 35 from the original length 36, illustrated in FIG. 6, to the deformed length 37, illustrated in FIG. 7, will be a function of the displacing force applied to the probe 20 by contraction of the clotting blood sample 50, the position of the portion 45 of the support arm 28 at which pivoting occurs relative to the angled portion 27 and the attachment end 23, and the spring constant of the spring element 35. Alternately, the optical instrument 60 may be used to determine the displacement of the probe 20 as a difference between an originally aligned gradation 62 and of an adjacent gradation aligned therewith after displacement of the probe 20. The size and shape of the probe 20, and the size of the wetted portion 24 of the probe 20 also affect the magnitude of the force applied to the probe 20 by contraction of the clotting blood sample 50.

It will be advantageous for embodiments of an apparatus 10 for measuring the capacity of a blood sample 50 to clot to be portable and compact. The components of the embodiments of the apparatus 10 discussed above in connection with FIGS. 2-7 can be optimized to satisfy the need for miniaturization. It will also be advantageous for embodiments of an apparatus 10 for measuring the capacity of a blood sample 50 to clot to be highly sensitive to very small displacing forces/displacements of any moving components that are displaced by the forces imparted to the probe 20. The embodiments of the apparatus 10 discussed below are adapted for miniaturization and for reliably sensing displacements of the wetted portion 24 of the probe 20 resulting from forces applied by the clotting blood sample 50.

Figure 8:
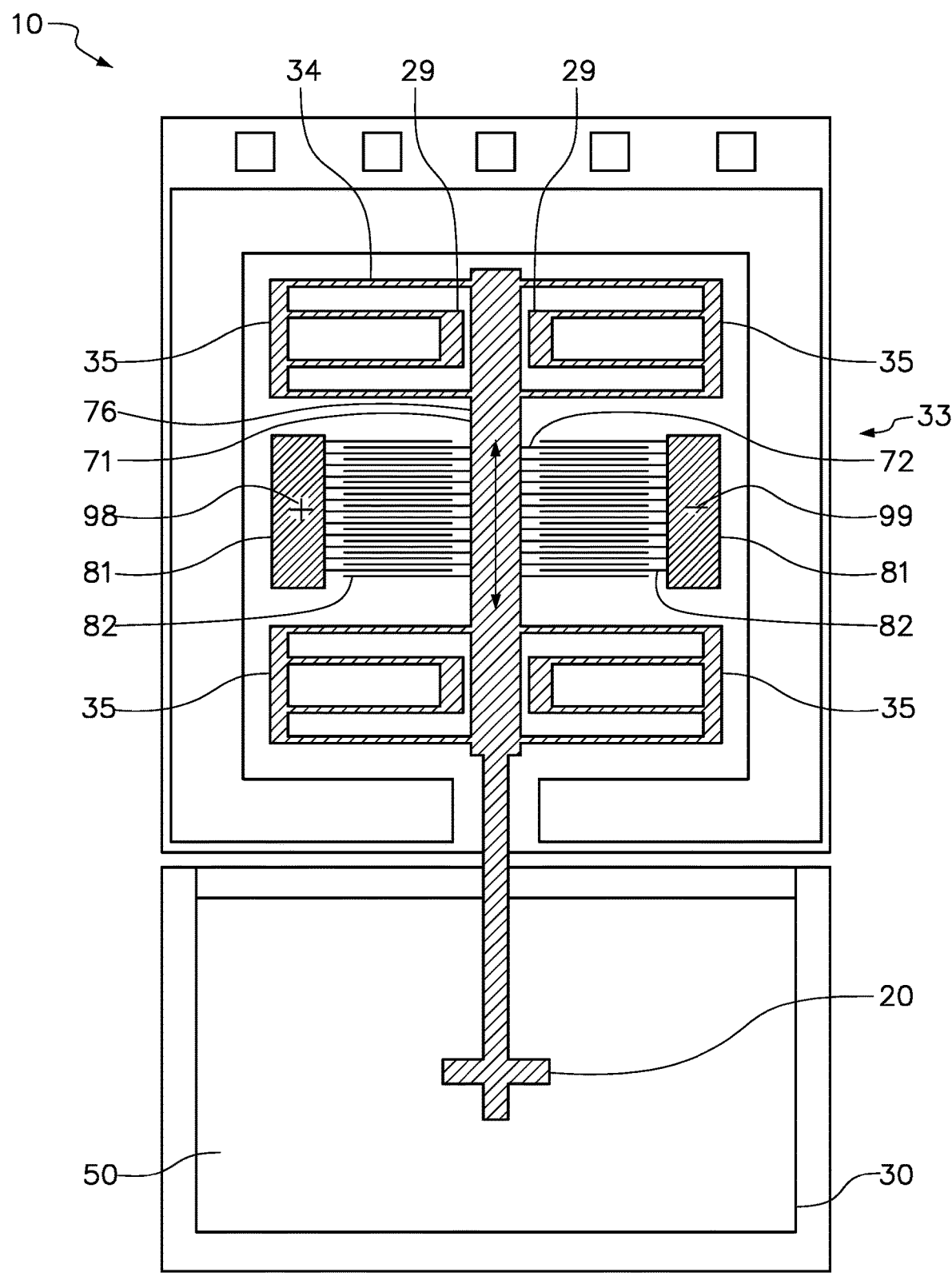
FIG. 8 is an elevational view of an embodiment of an apparatus for determining the capacity of a blood sample to clot, the apparatus including a variable capacitance displacement sensor.

FIG. 8 is an elevational view of an embodiment of an apparatus 10 of the present invention for determining the capacity of a blood sample 50 to clot. The apparatus 10 of FIG. 8 includes a well 30 for receiving a blood sample 50, a probe 20, a plurality of probe supports 29 and a plurality of spring elements 35 with legs 34 intermediate the probe 20 and the plurality of probe supports 29. The embodiment of the apparatus 10 of FIG. 8 includes a variable capacitance displacement sensor 33 disposed intermediate the probe 20 and the plurality of probe supports 29. The variable capacitance displacement sensor 33 includes a moving assembly 71 having a center mast 76 from which a plurality of moving fins 72 extend and a pair of stationary assemblies 81 from which a plurality of stationary fins 82 extend. The plurality of moving fins 72 supported on the moving assembly 71 are disposed in an interdigitated arrangement with the plurality of stationary fins 82 supported on the pair of stationary assemblies 81. A current, represented by the positive sign 98 and the negative sign 99, is applied across the pair of stationary assemblies 81. This arrangement results in a capacitor that temporarily stores electrical energy in an electric field around the plurality of moving fins 72 and the plurality of stationary fins 82. Factors affecting the electric field developed as a result of the current being applied include the surface area of the plurality of moving fins 72 and the plurality of stationary fins 82, the number of the plurality of moving fins 72 and the plurality of stationary fins 82 and the width of the gap between them it will be understood that the greater the surface area, the greater the number of fins and the smaller the gap, the greater the capacitance will be for a given current.

The variable capacitance displacement sensor 33 of FIG. 8 is variable because a small displacement of the plurality of moving fins 72 relative to the interdigitated plurality of stationary fins 82 changes the electronic behavior of the displacement sensor 33 by changing the electronic interaction between the plurality of moving fins 72 relative to the plurality of stationary fins 82, and the change can be measured and correlated to the displacement of the plurality of moving fins 72 relative to the stationary fins 82. When there is a non-variable potential across the conductors (e.g., when a capacitor is attached across a steady source of electrical potential such as, for example, a battery), an electric field develops across the dielectric, causing positive charge "+" to collect on one of the plurality of moving fins 72 and the plurality of stationary fins 82 and negative charge "−" to collect on the other of the plurality of moving fins 72 and the plurality of stationary fins 82. The measurement of the change in the capacitance properties of the sensor 33 as a result of the displacement of the plurality of moving fins 72 and the plurality of stationary fins 82 can be correlated to the magnitude of displacement of the probe 20 and to the capacity of the blood sample 50 to clot.

Figure 9:
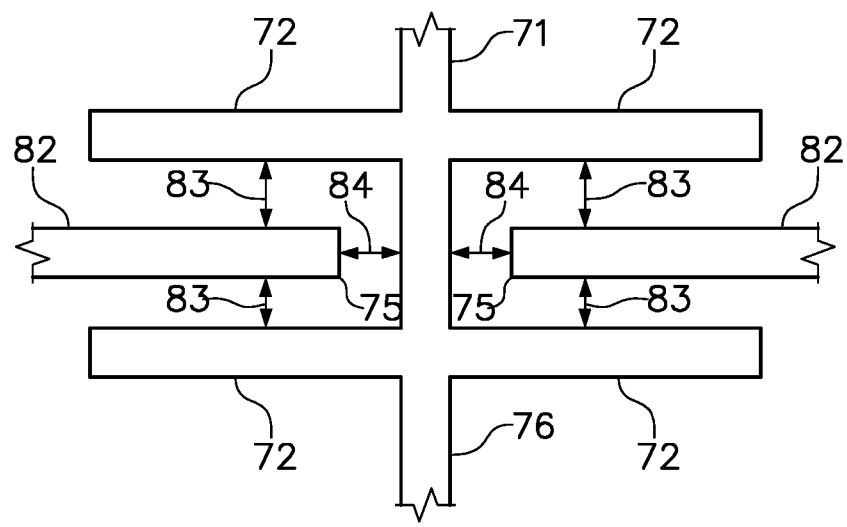
FIG. 9 is an enlarged view of a portion of the variable capacitance displacement sensor of the apparatus of FIG. 8 showing a pair of adjacent fins supported on a moving assembly of the displacement sensor and a fin supported on a stationary assembly of the displacement sensor disposed intermediate the fins of the moving assembly in an original position.

FIG. 9 is an enlarged view of a portion of a variable capacitance displacement sensor 33 of the apparatus 10 of FIG. 8 showing two pairs of adjacent moving fins 72 supported on a moving assembly 71 intermediate a pair of adjacent stationary fins 82 on a stationary assembly 81 of the displacement sensor 33 with a single stationary fin 82 supported on the stationary assembly 81 in an original position disposed between each member of each pair of moving fins 72. FIG. 9 illustrates that a first gap 83 between each moving fin 72 and the adjacent stationary fin 82, and a second gap 84 between an end 75 of each moving fin 72 and the center mast 76 of the moving assembly 71.

Figure 10:
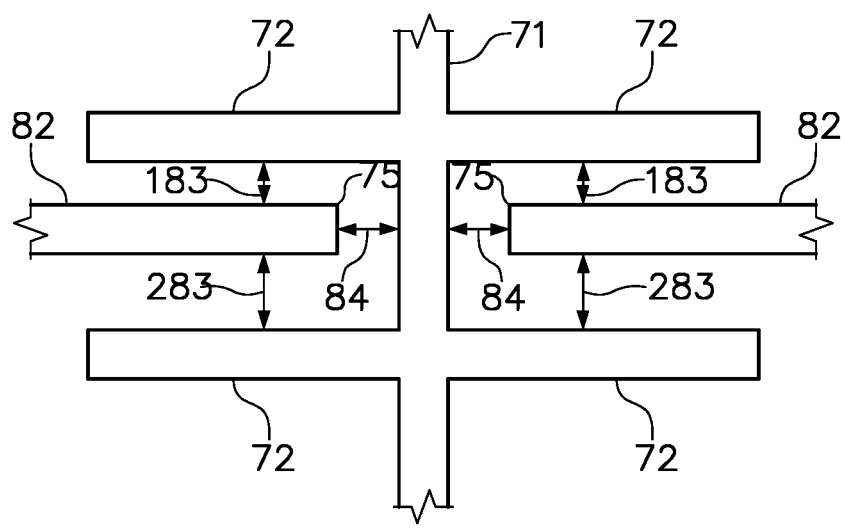
FIG. 10 is the enlarged view of FIG. 9 after the pair of fins of the moving assembly are displaced downwardly relative to the fin of the stationary assembly by a contractile force applied by the clotting blood sample to the wetted portion probe.

FIG. 10 is the enlarged view as is FIG. 9 after the pair of moving fins 72 of the moving assembly 71 are displaced relative to the stationary fins 82 of the stationary assembly 81 by contraction of a clotting blood sample 50 (not shown in FIG. 10) to the probe 20 of the displacement sensor 33. While the gaps 84 between the ends 75 of the stationary fins 82 and the center mast 76 are unchanged by the movement of the moving fins 72, the stationary fins 82 are no longer equidistant from the adjacent moving fins 72 and the asymmetrical position of the stationary fins 82 relative to the adjacent pair of moving fins 72 are represented by the new gaps 183 and 283 above and below the stationary fins 82, respectively. This new arrangement alters the electronic performance of the variable capacitance displacement sensor 33 to change from its original performance associated with the positions of the plurality of moving fins 72 and the plurality of stationary fins 82 reflected in FIG. 9. The modified electronic performance of the displacement sensor 33 can be measured and correlated to a displacement of the probe 20 of the apparatus 10 that produces the measured change.

The plurality of spring elements 35 illustrated in FIG. 8 as supporting the movable assembly 71 of the apparatus 10 are a plurality of folded beam springs. These spring elements 35 cooperate to accommodate linear movement of the probe 20 and to thereby prevent interference or contact between components of the moving assembly 71 and the stationary assembly 81.

Figure 11:
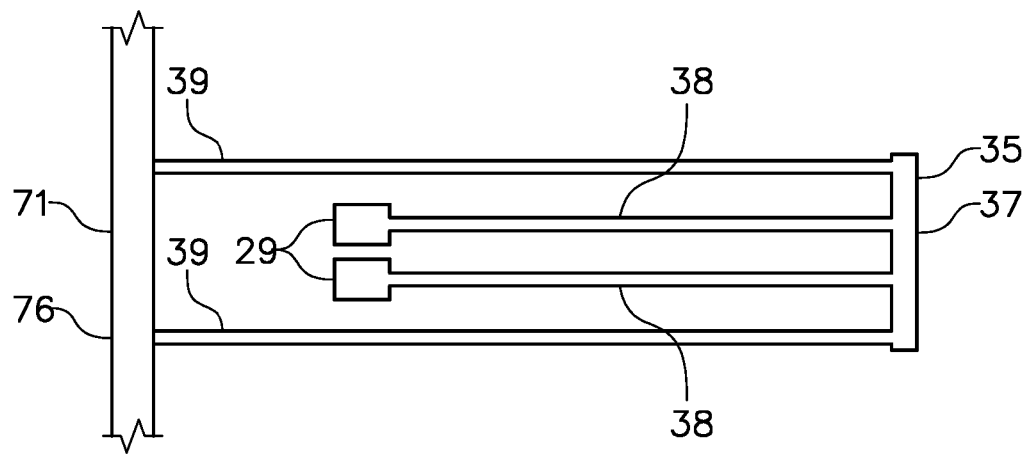
FIG. 11 is an enlarged view of a portion of the displacement sensor of FIG. 8 showing a spring element disposed intermediate a plurality of probe supports and a center mast of the moving assembly of the displacement sensor.

FIG. 11 is an enlarged view of a portion of FIG. 8 showing a spring element 35 disposed intermediate a plurality of probe supports 29 and a center mast 76 of the moving assembly 71 of the displacement sensor 33 of FIG. 8. The center mast 76 of the moving assembly 71 is connected to the probe 20. FIG. 11 illustrates an original position of the spring element 35 and the center mast 76 supported thereby. The spring element 35 of FIG. 11 includes a first leg 38 extending between each probe support 29 and a stabilizer 37 and a pair of second legs 39 extending between the stabilizer 37 and the center mast 76 of the moving assembly 71. The first legs 38 and the second legs 39 both connect to the stabilizer 37 and to the center mast 76 at generally right angles.

Figure 12:
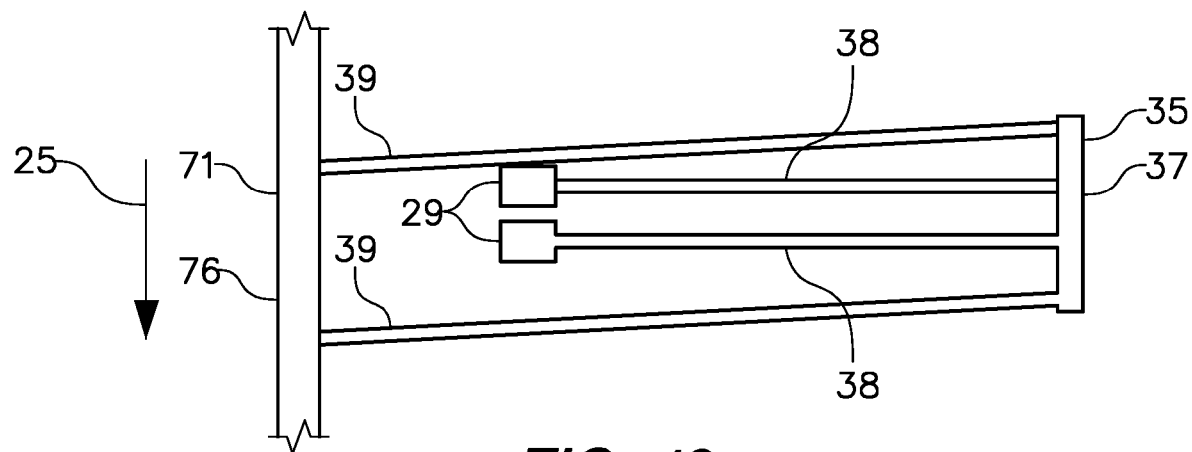
FIG. 12 is the view of the spring element of FIG. 11 after elastic deformation resulting from a clotting blood sample (not shown) being introduced into the well (not shown) of the apparatus of FIG. 8 and the contractile displacing force being applied by the clotting blood sample to the wetted portion of the probe (not shown) to elastically deform the spring element.

FIG. 12 is the view of the spring element 35 of FIG. 11 after a blood sample 50 (not shown) is introduced into the well 30 (not shown) of the apparatus 10 of FIG. 8 and a displacing force is applied by the clotting blood sample 50 to the wetted portion 24 of the probe 20 (not shown). The center mast 76, which is connected to the probe 20, is displaced downwardly in the direction of arrow 25. The first legs 38 and the second legs 39 are deformed from their previous configuration to accommodate movement of the center mast 76 relative to the probe supports 29.

Figure 13:
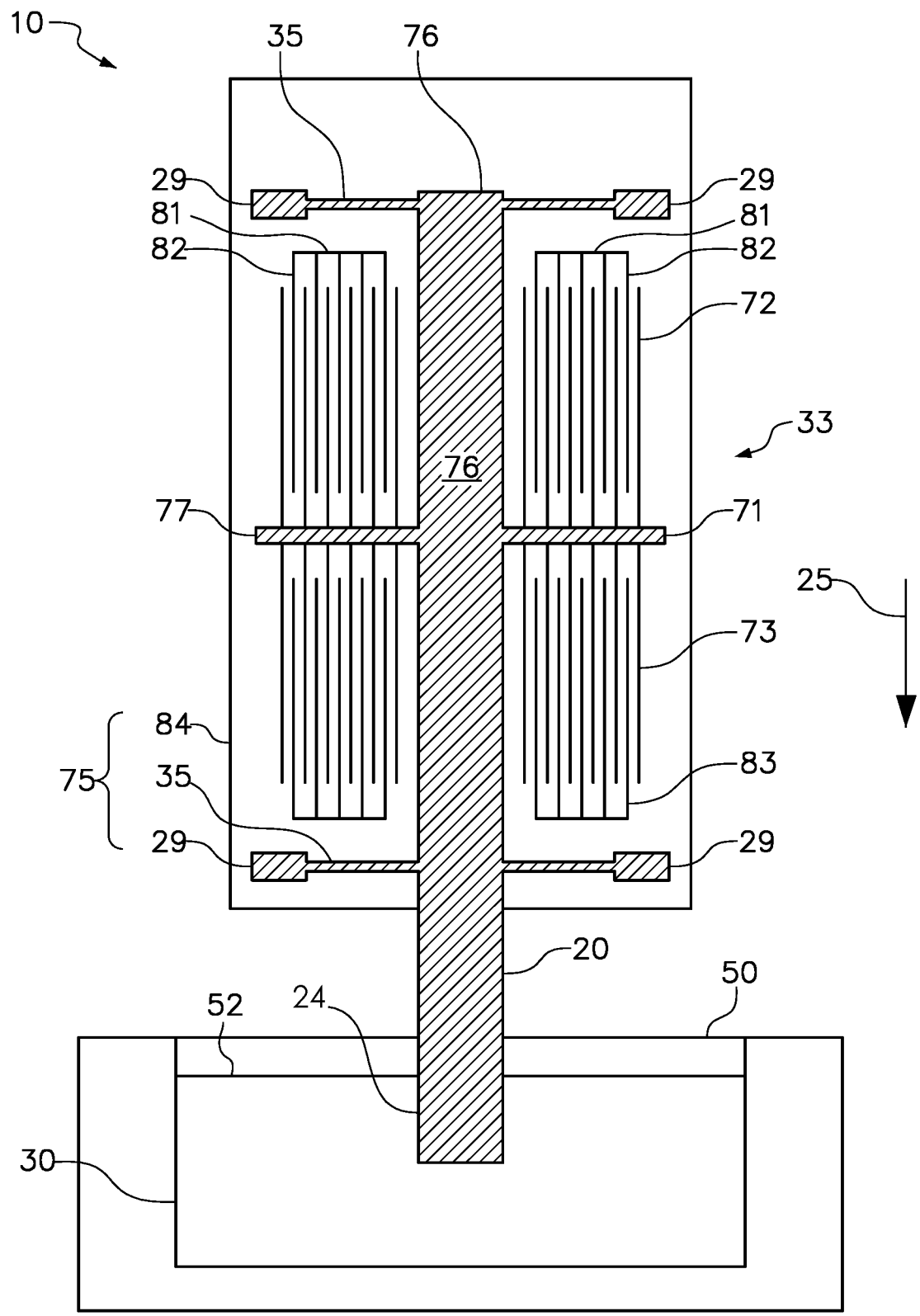
FIG. 13 is an elevational view of an alternative embodiment of an apparatus for determining the capacity of a blood sample to clot, the apparatus including an alternate version of a variable capacitance type displacement sensor.

FIG. 13 is an elevational view of an alternative embodiment of an apparatus 10 for determining the capacity of a blood sample 50 to clot. The apparatus 10 of FIG. 13 comprises a well 30 to receive a blood sample 50 up to blood interface 52, a probe 20 supported with a wetted portion 22 in the well 30 and a variable capacitance displacement sensor 33. The variable capacitance displacement sensor 33 includes a movable assembly 71 including a center mast 76 connected to the probe 20, a plurality of lateral supports 77 extending from the center mast 76, a plurality of moving fins 72 extending upwardly from the plurality of lateral supports 77, a plurality of moving fins 73 extending downwardly from the plurality of lateral supports, and a plurality of spring elements 35 disposed intermediate the center mast 76 and the probe supports 29. The apparatus 10 of FIG. 13 further includes stationary assemblies 81 having a plurality of downwardly extending stationary fins 82 in an interdigitated arrangement with the upwardly extending fins 72 of the moving assembly 71, and a plurality of upwardly extending stationary fins 83 in an interdigitated arrangement with the downwardly extending fins 73 of the moving assembly 71. It will be understood that a downwardly directed movement of the moving assembly 71 will further insert the plurality of downwardly extending fins 73 of the moving assembly 71 into the interdigitated positions relative to the plurality of upwardly extending fins 83 of the stationary assembly 81 while, at the same time, withdrawing the plurality of upwardly extending fins 72 of the moving assembly 71 from the interdigitated positions relative to the plurality of downwardly extending stationary fins 82 of the stationary assembly 81. This asymmetrical impact of movement of the moving assembly 71 on the extent to which the plurality of fins overlap can be used to enhance the sensitivity of the sensor 33 of the apparatus 10 to movement of the probe 20.

FIGS. 8 and 13 include variable capacitance displacement sensors 33 that can be used to detect and measure displacement of the probe 20 resulting from the introduction of a blood sample 50 into a well 30. For example, but not by way of limitation, the variable capacitance displacement sensors 33 in these embodiments may be charged at a known current, the time required to obtain a predetermined voltage can be measured, and this process can be repeated several times per second before, during and after probe 20 displacement as it is acted upon by contraction of the clotting blood sample 50.

Figures 14, 15:
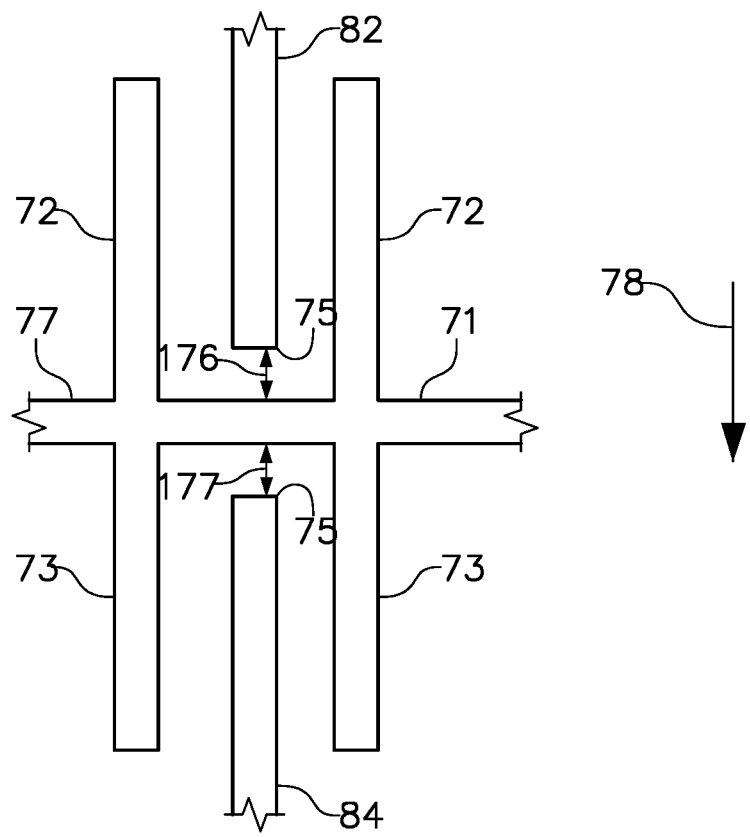
FIG. 14 is an enlarged view of a portion of the variable capacitance displacement sensor of the apparatus of FIG. 13 showing a pair of upwardly extending stationary fins and an adjacent pair of downwardly extending stationary fins supported on a lateral support of a stationary assembly of the displacement sensor with a downwardly extending moving fin and an upwardly extending moving fin supported on a moving assembly of the displacement sensor.
FIG. 15 is the enlarged view of FIG. 14 after the upwardly extending fins and the downwardly extending moving fins of the moving assembly are displaced downwardly to a displaced position as a result of a displacing force being applied to the wetted portion of the probe (not shown) by a clotting blood sample (not shown).

FIG. 14 is an enlarged view of a portion of a variable capacitance displacement sensor 33 of the apparatus of FIG. 13 showing a pair of upwardly extending moving fins 72 and an adjacent pair of downwardly extending moving fins 73 supported on a lateral support 77 of a moving assembly 71 of the displacement sensor 33 with a downwardly extending stationary fin 82 and an upwardly extending stationary fin 84 supported on the stationary assembly 81 of the displacement sensor 33. The downwardly extending stationary fin 82 is disposed between a pair of upwardly extending moving fins 72 in an original position, and the upwardly extending stationary fin 84 is disposed between a pair of downwardly extending moving fins 73 in an original position.

FIG. 15 is the enlarged view of FIG. 14 after the downwardly extending moving fins 73 of the moving assembly 71 are displaced to a displaced position as a result of a displacing force being applied to the probe 20 (not shown) by a clotting blood sample 50 (not shown). The displacement of the moving assembly 71 relative to the stationary assembly 71 results in the upwardly extending stationary fin 84 extending further between the downwardly extending moving fins 73 in the interdigitated position and in the upwardly extending moving fins 72 being withdrawn from the straddling position about the downwardly extending stationary fins 82. The gap 176 between the end 75 of the downwardly extending stationary fin 82 and the lateral support 77 is narrower and the gap 177 between the upwardly extending stationary fin 84 and the lateral support 77 is wider relative to the relative positions shown in FIG. 14.

The capacitance of a variable capacitance displacement sensor 33 is affected by, among other factors, the amount of surface area between two adjacent fins or plates of a capacitor and the proximity between the fins or plates. FIG. 15 illustrates how the amount of overlap, or surface area, between the upwardly extending moving fins 72 and the downwardly extending stationary fin 82 has increased, and how the overlap, or adjacent surface area, between the downwardly extending moving fins 73 and the upwardly extending stationary fin 84 has decreased, as a result of the displacement of the probe 20 (not shown) to which the moving assembly 71 is connected. This arrangement may be particularly advantageous for use in a displacement sensor 33 for detecting a small displacement and for producing a signal corresponding to the displacement. It will be understood that, to utilize this effect, the moving assembly 71 may need to be bifurcated (not shown) so that the upwardly extending moving fins 72 are conductively isolated from the downwardly extending moving fins 73.

Figure 16:
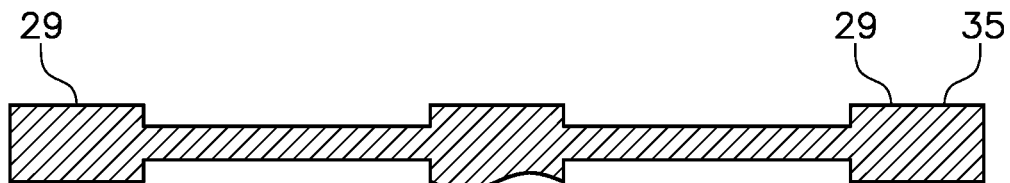
FIG. 16 is an enlarged view of one of the spring elements and a pair of probe supports of the apparatus of FIG. 13 supporting a center mast (not shown) of the variable capacitance displacement sensor.

FIG. 16 is an enlarged view of one of the spring elements 35 of FIG. 13 supporting a center mast 76 of the variable capacitance displacement sensor 33 (not shown). The center mast 76 of the variable capacitance displacement sensor 33 (not shown) is illustrated as being coupled to the spring element 35 near its center. The spring element shown in FIG. 16 is a beam spring.

Figure 17:
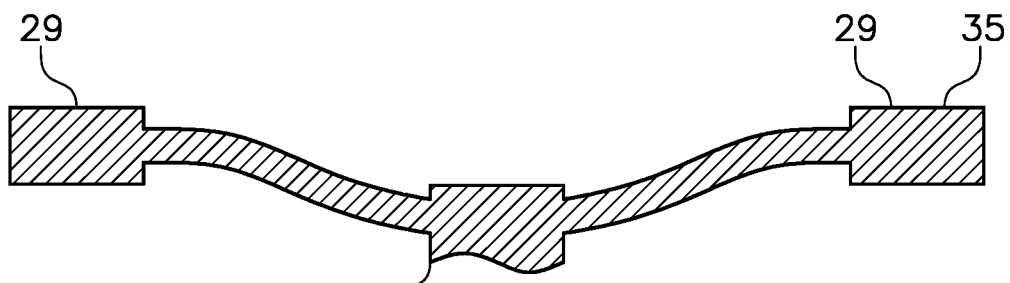
FIG. 17 is the enlarged view of the spring element of FIG. 16 after deflection by a displacing force applied to the wetted portion of the probe (not shown) by a clotting blood sample introduced into the well (not shown) of the apparatus.

FIG. 17 is a view of the spring element 35 of FIG. 16 after deflection by a downwardly directed displacing force applied to the probe 20 (not shown) by a clotting blood sample 50 (not shown) introduced into the well 30 (not shown) of the apparatus 10. The center mast 76 of the variable capacitance displacement sensor 33 (not shown) is illustrated as being coupled to the spring element 35 near its center. The spring element 35 shown in FIG. 17 is a beam spring and is supported by pivoting probe supports 29.

Figure 18:
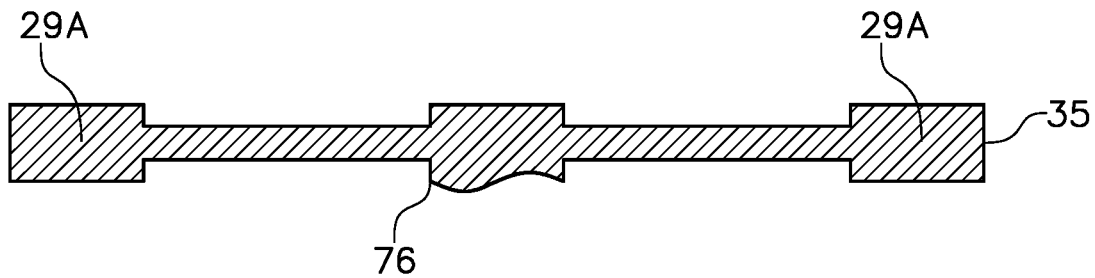
FIG. 18 is an enlarged view of a spring element for supporting a wetted member of an embodiment of the apparatus of the present invention having pivoting probe supports to accommodate deflection of the spring element as a result of a displacing force being applied to the wetted portion of the probe.

FIG. 18 is an enlarged view of a spring element 35 of FIG. 13 having pivoting probe supports 29A to accommodate deflection of the spring element 35. The pivoting probe supports 29A are pivoted to enable the probe supports 29A to rotate as deflection of the spring element 35 occurs.

Figure 19:
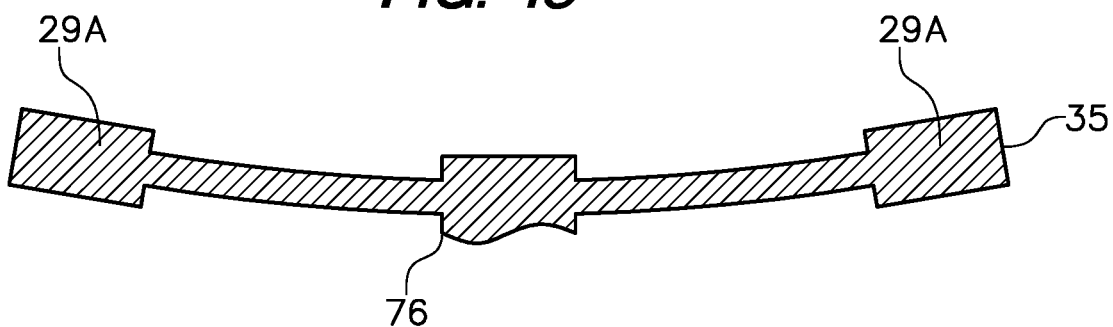
FIG. 19 is enlarged view of the spring element of FIG. 18 after deflection of the spring element causes the pivoting probe supports to rotate from their original positions.

FIG. 19 is a view of the spring element 35 of FIG. 18 after deflection of the spring element 35 to cause the pivoting probe supports 29A to rotate from their original positions to accommodate deflection of the spring element 35.

Figure 20:
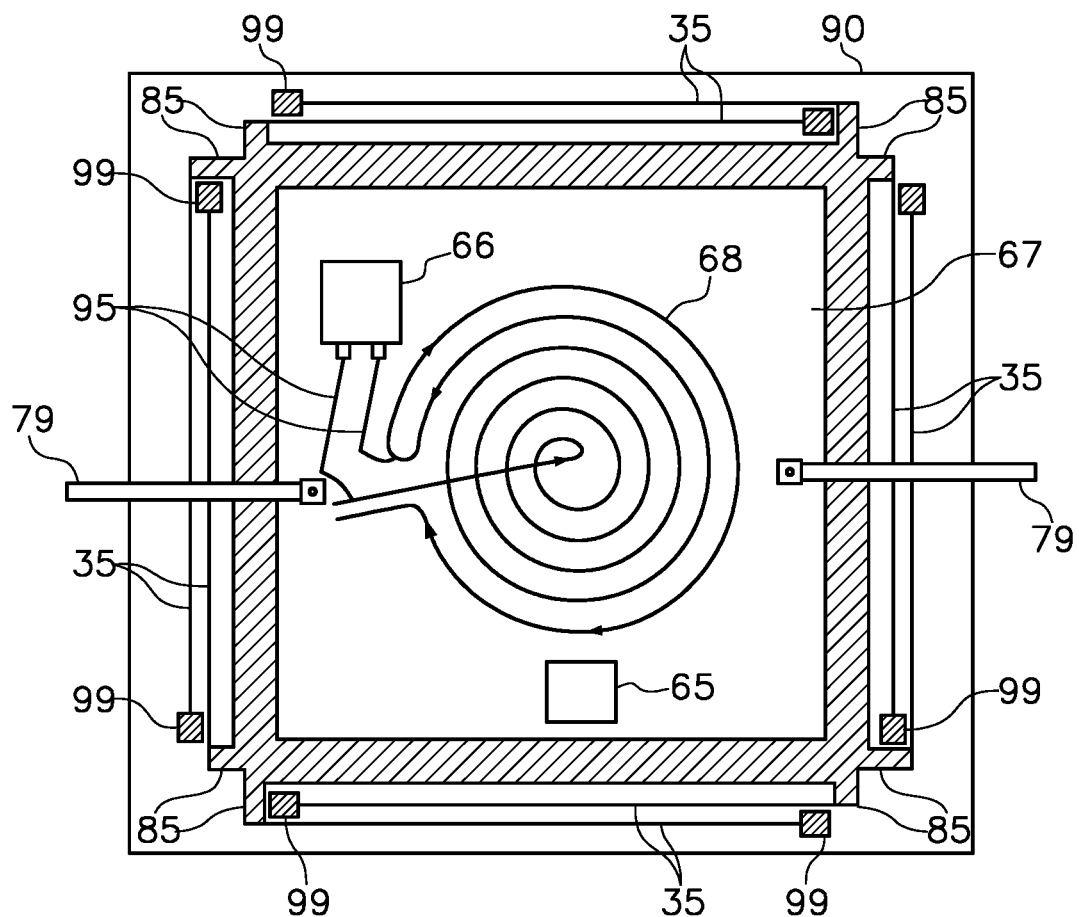
FIG. 20 is a plan view of an alternative embodiment of an apparatus of the present invention to determine the capacity of a blood sample to clot, the apparatus including an eddy current type displacement sensor.

FIG. 20 is a plan view of an alternative embodiment of an apparatus 10 to determine the capacity of a blood sample 50 to clot. (FIG. 23, discussed below, is a related elevation view of the apparatus 10 of FIG. 20, but with the plurality of cantilevered spring elements 35 removed (except the foot 99 of two of the cantilever spring elements 35) from between the target support 90 and the coil support 67 to better reveal the structures of the apparatus 10.)

Figure 23:
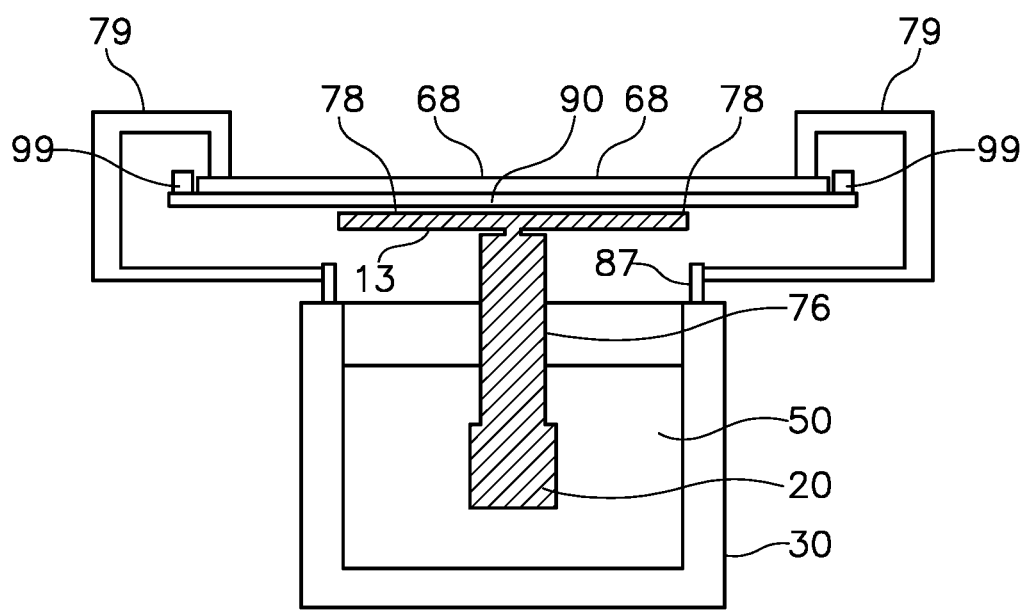
FIG. 23 is an elevation view of the embodiment of the apparatus of FIG. 20 showing the metal target disposed underneath the coil and the coil support and in close proximity to the coil so that the eddy currents produced as a result of a current from the current source coupled to the coil are affected by the proximity of the metal target to the coil.

The embodiment of the apparatus 10 of FIG. 20 includes a coil support 67 supporting an electrical coil 68 thereon in a stationary position relative to the well 30 (not shown in FIG. 20—see FIG. 23) there below. The coil 68 is connected to a current source 66 such as, for example, a battery. The coil 68, which may be supported near a center of the coil support 67, and the coil support 67 are together supported by one or more coil support arms 79 that are connected to the well 30 at a first end 87 (not shown in FIG. 20—see FIG. 23). The coil support 67 also supports a thigh portion 85 of each of a plurality of cantilevered spring elements 35 secured between the coil support and a metal target 13 in a "crab legged" arrangement. FIG. 20 shows each of the plurality of cantilever spring elements 35 includes a thigh portion 85 at a first end and a foot 99 at a second end. Only the foot 99 of two cantilever spring elements 35 are shown in FIG. 23 to better reveal the relative positions of the coil support 67 and the target support 90. The foot 99 of each of the plurality of cantilever spring elements 35 is coupled to the target support 90 that, in the view of FIG. 20, is larger than the metal target 13 connected to the target support 90 at connectors 78. The metal target 13 is connected to a probe 20 that is suspended within a well 30 (see FIG. 23). The plurality of spring elements 35 illustrated in FIG. 20 provide for movement of the metal target 13 and the target support 90 of FIG. 23 relative to the coil 68 and the coil support 67.

It will be understood from FIGS. 20 and 23 that the coil support arms 79 support the coil 68, the coil support 67, the target support 90 and the metal target 13, and that the metal target 13 is movable relative to the coil support arms 79 and the coil 68 by flexure of the plurality of cantilever spring elements 35. This arrangement enables the metal target 13 to be displaced relative to the coil 68 and to thereby produce a detectable response in an eddy current produced by the coil 68 upon energization by the current source 66. At the same time, the embodiment of the apparatus 10 and method illustrated in FIGS. 20 and 23 eliminates the interference with the displacement of the probe 20 that may in other embodiments be caused by the electrical leads 95 that deliver current from the power source 66 to the coil 68. With the versions of the variable capacitance displacement sensor of the embodiments of FIGS. 8 and 13, the electrical leads connected to provide a current to the variable capacitance displacement sensor (represented by the "positive" and "negative" signs at reference numerals 98 and 99 on FIG. 8), the electrical leads will present an unwanted resistance to the downwardly displacement of the probe 20. The embodiment of the apparatus 10 and method illustrated in FIGS. 20 and 23, however, enables the detection and measurement of the displacement of the probe 20 without impairing the movement of the probe 20 with electrical leads 95, which extend from the coil 68 to the power source 66, neither of which are required to move for the apparatus 10 to function.

The introduction of a blood sample 50 into the well 30 of FIG. 23 to contact the probe 20 produces a downwardly displacing force applied to a probe 20 by the clotting blood sample 50. The metal target 13 is supported from the coil support 67 by the plurality of spring elements 35 (see FIG. 20) disposed intermediate the metal target 13 and the coil support 67. The coil 68 and the coil support 67 together remain stationary, and eddy currents produced by the coil 68 as a result of the current provided by the current source 66 are detectable by an eddy current sensor 65 positioned in close proximity to the coil 68. The eddy currents will vary in response to the proximity of the metal target 13 to the coil 68, thereby enabling the displacement of the probe 20 resulting from the introduction of a blood sample 50 into the well 30 to be detected and measured by correlating changes in the eddy currents detected and measured by the eddy current sensor 65 to the displacement of the probe 20.

Figure 21:
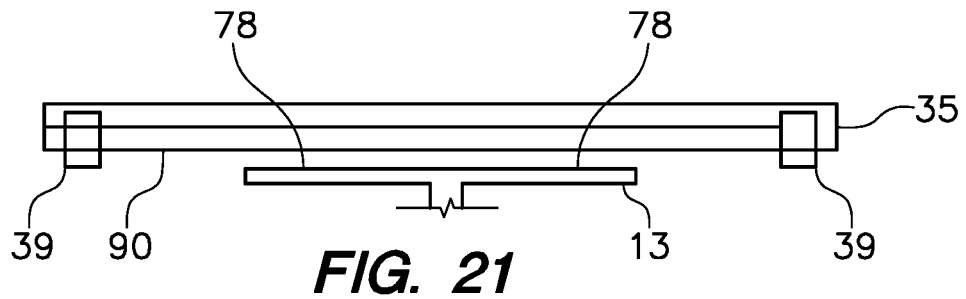
FIG. 21 is an illustration of a pair of opposed cantilevered spring elements of the type that may be used in embodiments of the apparatus of the present invention. These spring elements are illustrated in an original position prior to downward displacement of a wetted portion of a probe supported by the spring elements.

FIG. 21 is an illustration of a pair of cantilevered spring elements 35 of the apparatus 10 of FIG. 20 in an original position prior to the introduction of a blood sample 50 (not shown) into the well 30 (not shown). It will be noted that the metal target 13 that is connected to the probe 20 (not shown) is in an original position with the metal target 13 in very close proximity to the coil 68 on the coil support 67.

Figure 22:
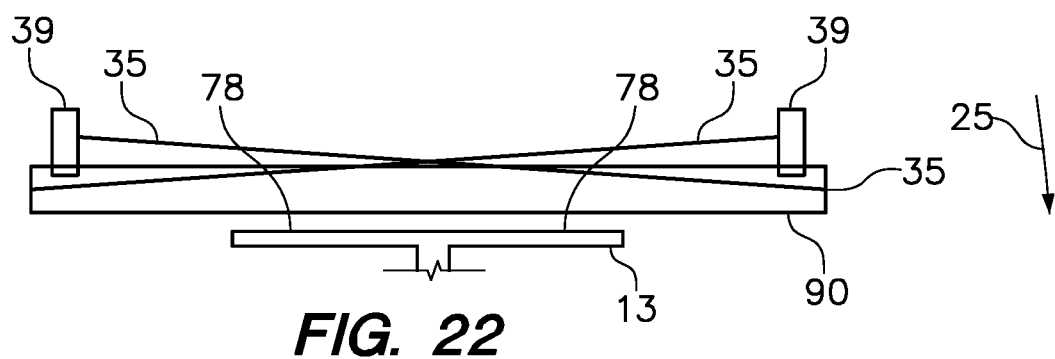
FIG. 22 is the illustration of the pair of opposed cantilevered spring elements of FIG. 21 after the cantilevered spring elements are elastically deformed in a manner that would occur if the metal target of FIG. 23 is downwardly displaced relative to the coil support by a displacing force applied to the wetted portion of the probe (not shown) of the apparatus by a clotting blood sample (not shown).

FIG. 22 is the illustration of the cantilever spring elements 35 of the apparatus 10 of FIG. 21 after the coil support 67 (not shown) is downwardly displaced by a displacing force applied to the probe 20 (not shown) of the apparatus 10 by the clotting blood sample 50 (not shown). It will be noted that the cantilever spring elements 35 of the apparatus 10 are together deflected to accommodate the downward displacement of the probe 20 (not shown) and the metal target 13 to which the probe 20 is attached. This movement of the metal target 13 relative to the coil 68 on the coil support 67 results in a variance in the eddy current in the coil 68 that is detectable and measureable by the eddy current sensor 65 disposed near the coil 68.

FIG. 23 is the elevation view of the apparatus 10 of FIG. 20 with the plurality of cantilever spring elements 35 removed to reveal the relative positions of the metal target 13 and the coil support 67. It will be noted that the metal target 13 is movable and in close proximity to the coil 67 so that the eddy currents produced when the current source 66 is coupled to the coil 68 are affected by the proximity of the metal target 13 to the coil 68. The metal target 13 is attached to the probe 20 and moves with the probe 20 as acted upon by the clotting blood sample 50 in the well 30, and the distance between the stationary coil 68 and movable metal target 13 there below can be detected and measured using ECS circuitry. A signal generator and output circuits may be used to amplify an output signal from the eddy current sensor 65 of FIG. 20. In one embodiment of the apparatus 10 and method of the present invention, the coil 68 may be supported on a coil support 67 such as, for example, a multi-layered printed circuit board comprising a ferromagnetic material. The coil 68 may be etched onto the coil support 67 in this embodiment. In one embodiment of the apparatus 10 and method of the present invention, a specific amount of amperage such as, for example, 1 milli-amp (mA), may be required to sustain a given current provided by the current source 66. As the metal target 13 is moved by the probe 20 and in response to the introduction of a blood sample 50 into the well 30 of the apparatus 10 in FIGS. 20 and 23, more or less current may be required to sustain and maintain the 1 mA set point. This is an example of a closed loop feedback circuit that may be used with one embodiment of the apparatus 10 of the present invention.

FIGS. 24, 25, 26 and 27 illustrate cross-sections of four alternatively-shaped probes 20 that may be used in embodiments of the present invention. Each of these probes 20 may enhance the displacing force applied to the probe 20 by the clotting of the blood samples 50 used with embodiments of the apparatus 10. These alternative probes 20 are not meant to be exhaustive of the wide variance of shapes of probes 20 that can be used with embodiments of the apparatus 10 of the present invention, but are instead provided as mere examples of cross-sections of probes 20 that may be used to enhance the displacing force applied to the probe 20 by the clotting and contraction of the blood sample 50.

Figure 24:
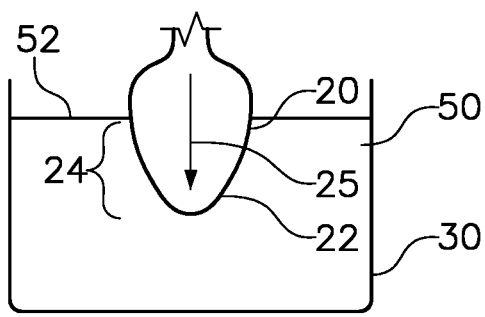
FIG. 24 illustrates a probe of an embodiment of the apparatus of the present invention having an exterior surface and a wetted portion contacted by a blood sample below an interface.

FIG. 24 illustrates a probe 20 having an exterior surface 22 and a wetted portion 24 contacted by a blood sample 50 below an interface 52. The probe 20 of FIG. 24 has a cross-section that is generally bulbous, with the wetted portion 24 being progressively diametrically smaller as it extends deeper into the blood sample 50 in the well 30.

Figure 25:
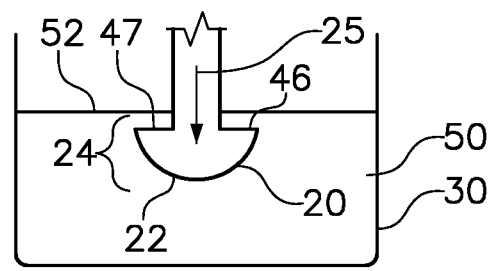
FIG. 25 illustrates a probe of an embodiment of the apparatus of the present invention having an exterior surface and a wetted portion immersed in a blood sample below an interface.

FIG. 25 illustrates a probe 20 having an exterior surface 22 and a wetted portion 24 immersed in a blood sample 50 below an interface 52. The probe 20 has a cross-section that is generally semi-circular with a domed portion disposed downwardly within the blood sample 50 which, like the probe 20 of FIG. 24, also includes a wetted portion 24 being progressively diametrically smaller as it extends deeper into the blood sample 50 in the well. It will be noted that the interface 52 in FIG. 25 is above the flattened portion 46 on an upwardly disposed surface 47 of the probe 20.

Figure 26:
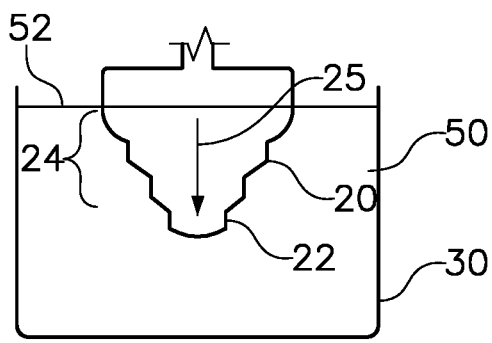
FIG. 26 illustrates a probe of an embodiment of the apparatus of the present invention having a corrugated exterior surface and a wetted portion immersed in a blood sample below an interface.

FIG. 26 illustrates a probe 20 having a more complex exterior surface 22 and a wetted portion 24 immersed in a blood sample 50 below an interface 52. The probe 20 has a staggered cross-section that "steps" radially as it extends deeper into the blood sample 50, with the wetted portion 24 being progressively diametrically smaller as it extends deeper into the blood sample 50 in the well 30.

Figure 27:
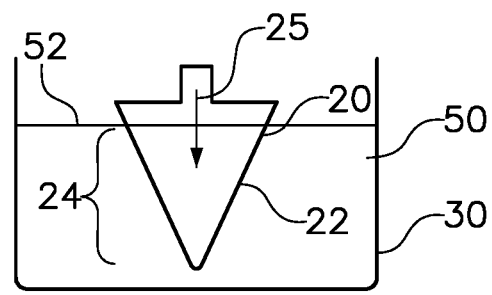
FIG. 27 illustrates a probe of an embodiment of the apparatus of the present invention having a conical exterior surface and a wetted portion immersed in a blood sample below an interface.

FIG. 27 illustrates a probe 20 having an exterior surface 22 and a wetted portion 24 immersed in a blood sample 50 below an interface 52. The probe 20 has a cross-section that is generally frusto-conical, with the wetted portion 24 being progressively diametrically smaller as it extends deeper into the blood sample 50 in the well 30. The cross-sections of each of the probes 20 illustrated in FIGS. 24-27 have more wetted portion 24 surface area below the interface 52 that is disposed downwardly than wetted portion 24 surface area above the interface 52 that is disposed upwardly, and as fibrins forming within the clotting blood sample 50 adhere to the wetted portion 24 of the exterior surface 22 of the probe 20, this accentuates the displacing force that is applied to the probe 20 in the direction of the arrow 25.

It will be understood that the probes 20 of FIGS. 24-27 are mere examples of probes 20 that may be used in embodiments of the apparatus 10 of the present invention or to implement embodiments of the method of the present invention, and are not intended to be limiting of the invention. As a general rule, a probe 20 may be shaped to enhance the displacing force applied to the probe 20 by the contraction of the clotting blood sample 50. For example, a cumulative downwardly disposed surface area of the probe 20 that is contacted by the blood sample 50 may be substantially greater than the cumulative upwardly disposed surface area of the probe 20 that is contacted by the blood sample 50.

Figure 28:
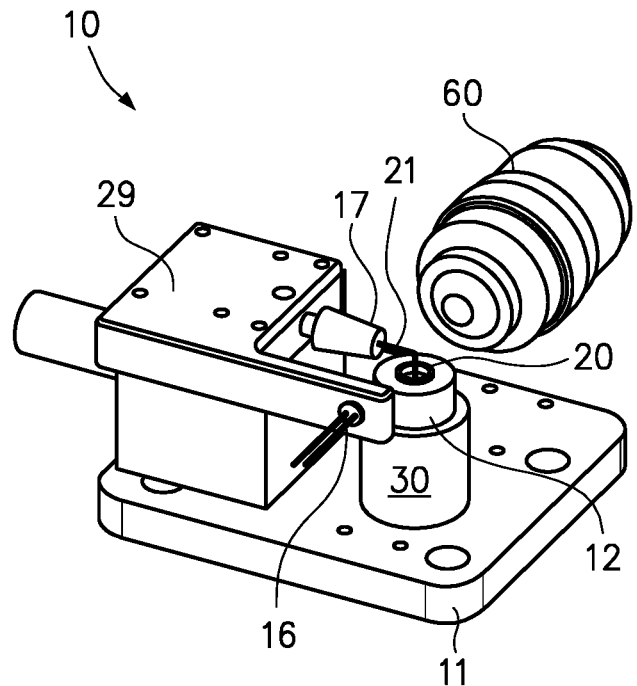
FIG. 28 is an elevation view of an embodiment of the apparatus of the present invention that includes a well disposed on a base, a chuck for supporting the probe within the well and an optical instrument type displacement sensor.

FIG. 28 is an elevation view of an embodiment of the apparatus 10 of the present invention that includes a well 30 disposed on a base 11. The well 30 surrounds a vial 12 (not shown in FIG. 28) that contains a blood sample 50 (not shown in FIG. 28). The well 30 may insulate the vial 12 to prevent unwanted effects of ambient temperature changes. The well 30 may include an embedded closed loop heater (not shown) and/or a thermocouple (not shown) to enable the temperature of the blood sample 50 to be controlled and/or monitored. The well 30 may comprise aluminum or various other materials. The vial 12 may comprise various materials such as, for example, glass, plastic, Pyrex® or other materials, and may be reusable after cleaning or it may be disposable. The apparatus 10 of FIG. 28 comprises an optical instrument 60 displacement sensor disposed to enable the precise optical measurement of the displacement of the probe 20 resulting from contraction of the clotting blood sample 50 (not shown). The apparatus 10 of FIG. 28 further comprises a light emitting diode (LED) light source 16 aligned with the probe 20 and the optical element 60 to enable precise detection of small displacement of the probe 20.

The probe 20 of the apparatus of FIG. 28 is releasably supported by chuck 17 coupled to the probe support 29. The probe 20 comprises a wire portion 21 that attaches to an enlarged wetted portion 24 (not shown in FIG. 28) supported within the vial 12 (not shown) within the well 30. The chuck 17 may, for example, be one of rotatable and retractable to grip and releasably grip the wire portion 21 of the probe 20. The wire portion 21 of the probe 20 may comprise various materials such as, for example, nickel or stainless steel, and may be either reusable after cleaning or disposable.

Figure 29:
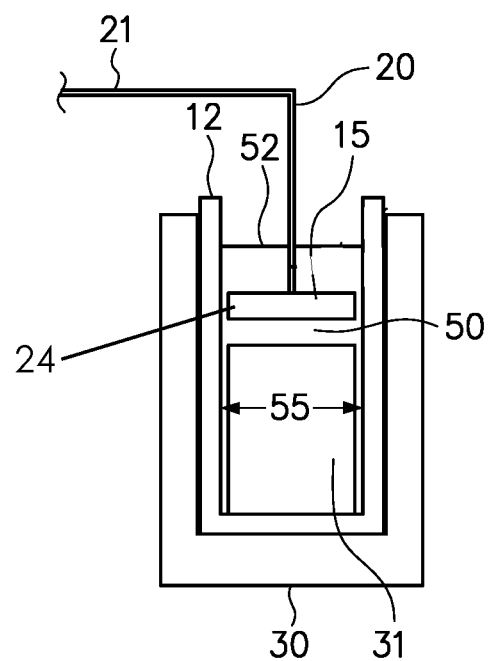
FIG. 29 is an enlarged sectional view of the well of FIG. 28 and of a vial disposed therein intermediate the well and a blood sample with a cantilevered probe supported within the well.

FIG. 29 is an enlarged sectional view of the well 30 of FIG. 28 and the vial 12 disposed therein. The vial 12 shown in FIG. 29 contains a lower member 34 which may comprise various materials such as, for example, acrylic, and which may be circular to conform to the vial 12. The wire portion 21 of the probe 20 is releasably supported by the chuck 17 (not shown in FIG. 29). The probe 20 further includes a wetted member 24 that comprises an enlarged plate 15 that may be circular to conform to the vial 12. The plate 15 may comprise various materials such as, for example, acrylic, and is supported within the blood sample 50 and in a spaced-apart relationship with the lower member 31. The wetted member 24/plate 15 of the probe 20 is supported by the wire portion 21 of the probe 20 below the interface 52 of the blood sample 50 and is submerged within the blood sample 50 adjacent to the lower member 31. As discussed above in relation to FIGS. 2-7, the wire portion 21 of the probe 20 functions as an integral spring element in a cantilever mode.

Figure 30:
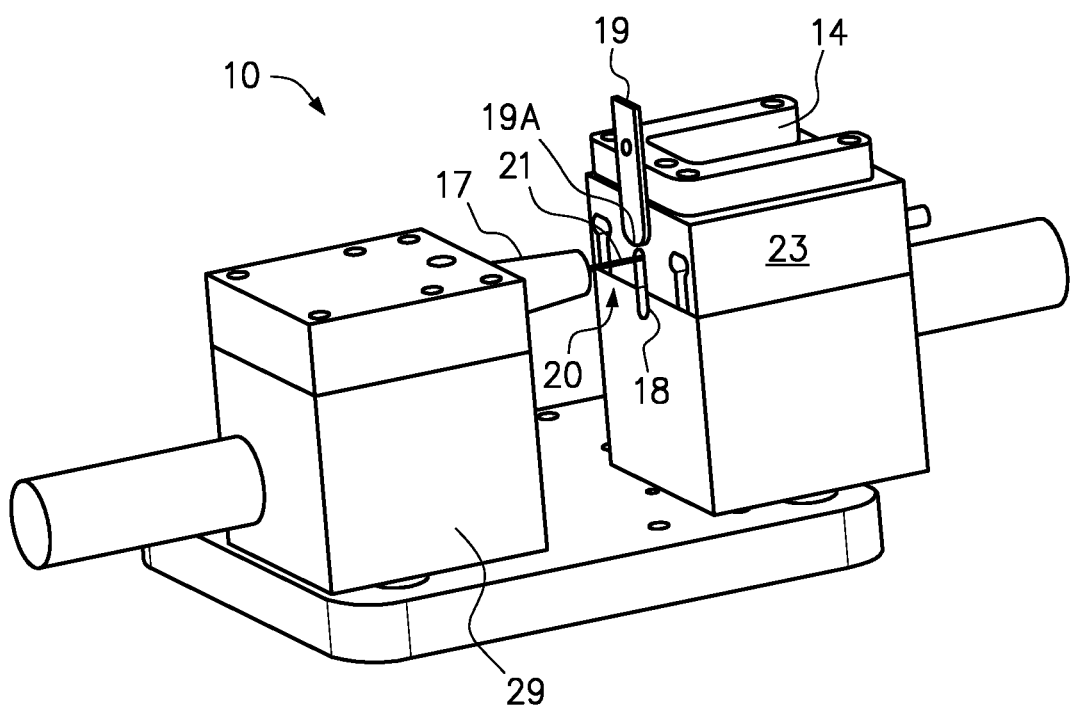
FIG. 30 is a perspective view of an embodiment of the apparatus of the present invention having a cantilevered probe support, a chuck releasably supporting a wire portion of the cantilevered probe, a well surrounding the vial (not shown) therein and a microelectromechanical (MEMS) device type displacement sensor engaging a wire portion of the probe and providing a signal corresponding to the sensed displacement of the probe to a piezoelectric adjustable positioning stage.

FIG. 30 is a perspective view of an embodiment of the apparatus 10 of the present invention having a probe support 29, a chuck 17 releasably supporting a probe 20, a well 30 surrounding the vial 12 (not shown) therein and a microelectromechanical (MEMS) device 19 type displacement sensor that can be used as a substitute for the optical element 60 and the LED source 16 illustrated in FIG. 28. The wire portion 21 of the probe 20 penetrates a vertical slot 18 in the well 30 so that downwardly displacement the wire portion 21, as discussed above in relation to FIGS. 5 and 7 (see arrow 25 in those drawings) will be unobstructed. The MEMS device 19 type displacement sensor may be secured to the well 30 by a bracket 14 to engage the wire portion 21 of the probe 20 and to measure the displacement thereof resulting from contraction of a blood sample 50. The MEMS device 19 type displacement sensor detects and measures one of the force imparted to and the resulting displacement of the probe 20 occurring as a result of the contraction of a clotting blood sample 50 (not shown) within the vial 12 (not shown). The MEMS device 19 type displacement sensor generates an electronic signal corresponding to the sensed displacement and/or force and may direct the signal to an adjustable piezoelectric positioning stage 23 or to a processor (not shown).

Contraction of the clotting blood sample 50 (not shown in FIG. 30) results in a downwardly directed displacing force applied to the wetted member 23/plate 15 (not shown—see FIG. 29) and to the connected wire portion 21 of the probe 20 and thereby causes a downwardly directed deflection of the cantilevered wire portion 21 of the probe 20 (within the slot 18) through an angle 21 (angle of displacement illustrated in FIG. 5). As an alternative to or in addition to the use of a MEMS device 19, the angle 21 of deflection of the wire portion 21 may be detected using an LED light source 16 which is attached to the adjustable piezoelectric positioning stage 23. Alternately, the LED light source 16 illuminates the wire portion 21 of the probe 20 and the downward displacement of the wire portion 21 of the probe 20 is imaged and tracked using an optical instrument 60 such as, for example, a 10× Nikon® microscope that is connected to an image recording device such as, for example, a Hitachi® KP-F120CL digital camera to record and preserve images. The images may be captured periodically such as, for example, at 3 second intervals, using a LabVIEW® edge detection software program. The deflection of the wire portion 21 of the probe 20 can be measured in, for example, pixels using the recorded images. A micro-grid can then be used to calculate the size of a single pixel at the focal length of the lens of the optical instrument 60 and the pixel information can be converted to microns. This data can be stored in a database allowing comparative statistics and further calculations using a processor connected thereto.

Returning to FIG. 29, the separation of the wetted portion 24/plate 15 of the probe 20 and the lower member 31 of the apparatus 10 and the surrounding vial 12 can vary. In one embodiment of the apparatus 10 of the present invention, the wetted portion 24/plate 15 and the lower member 31 are both circular and within the diameter range from 1 mm to 6 mm, and the vial 12 has a 7 mm inner diameter 55. In one embodiment of the apparatus 10 of the present invention, the volume of the blood sample 50 that is disposed between the wetted portion 24/plate 15 of the probe 20 and the lower member 31 may be, for example, 27 µL. In one embodiment of the apparatus 10 of the present invention, a thin layer of silicon oil is applied over the interface 52 at the top of the blood sample 50 to prevent unwanted evaporation of any volatile component within the blood sample 50 such as, for example, water.

The MEMS device 19 displacement sensor can be used as a force sensor. The force imparted to the probe 20 as a result of platelet contraction within the clotting blood sample 50 can be derived from displacement of the flexible wire portion 21 of the probe 20 (as shown in FIG. 5), as measured using the MEMS device 19, using the equation governing force generation for displacement of a cantilever:

$$F = (3\delta EI)/L^3$$

where F is force, $\delta$ is the wire portion 21 displacement, E is elastic modulus of the material of the wire portion 21 (e.g., nickel), I is the moment of inertia of the cross section of the wire portion 21 of the probe 20, and L is length of the wire portion 21 of the probe 20.

Validation of the force derivation obtained from measurement of the displacement of the wire portion 21 of the probe 20 using the embodiment of the apparatus 10 of FIG. 30 was verified using a MEMS device 19 type displacement/force sensor in conjunction with the piezoelectric adjustable positioning stage 23. The resolution of the piezoelectric adjustable positioning stage 23 was determined to be ±0.1 nm with 0.02% positioning accuracy, while resolution of the force sensing MEMS device 19 type displacement/force sensor was determined to be ±0.5 µN with a range of ±10,000 µN. The validation studies were conducted from 0 to 30 microns because this was the range of the average deflection recorded during assays using whole human blood for the blood sample 50.

The MEMS device 19 type displacement/force sensor was connected to the adjustable positioning stage 23 using bracket 14 to allow vertical translation in the z-axis. The tip 19A of the MEMS device 19 type displacement/force sensor is in contact with the wire portion 21 of the probe 20 at a position along the probe 20 that is distal to the chuck 17. The measured downward displacement of the piezoelectric adjustable positioning stage 23 caused an equal amount of deflection in the wire portion 21 of the probe 20, and the MEMS device 19 type displacement/force sensor measured the resultant force in Newtons. The force measured using the MEMS device 19 type displacement/force sensor was recorded and used to derive predicted wire portion 21 deflection, and this predicted deflection was correlated to actual deflection of the piezoelectric adjustable positioning stage 23. This test design modeled the force that is exerted on the wire portion 21 by a contracting blood sample 50 disposed between the wetted portion 24/plate 15 of the probe 20 and the lower member 31. Acrylic was the material used for the plate 15 and the lower member 31 for these tests.

Embodiments of the apparatus 10 of the present invention are used to characterize platelet mitochondrial function. One or more samples of human whole blood were collected by a licensed medical doctor from a healthy volunteer known to refrain from the taking of anticoagulant medications such as, for example, aspirin. Written informed consent of the donors was collected under an approved protocol from the Internal Review Board at the UT Health Science Center. Human whole blood was collected, by antecubital venipuncture, into vials 12 containing the anticoagulant sodium citrate (3.8%, applied at a 9:1 blood to citrate ratio). Platelet-rich plasma was then produced by centrifuging human whole blood treated with anticoagulant for 10 minutes at a centrifuge speed for providing 200×g. The resultant plasma suspension and platelet layer were removed, using a pipette, from the packed red blood cells (RBCs) and these platelets were added to whole blood samples. Platelet-poor plasma was then produced by centrifuging platelet-rich plasma for 15 minutes at a centrifuge speed for providing 3000×g, and then by removing the upper two-thirds of the centrifuged sample that contains the platelets. Platelet counts were determined for the samples and they were maintained at room temperature on a tilt-rocker prior to testing.

Embodiments of the apparatus 10 of the present invention may also be used to characterize clot contraction. The capacity of embodiments of the apparatus 10 of the present invention to characterize clot contraction properties was demonstrated by doing assays using whole blood, platelet-rich plasma and platelet-poor plasma samples. As a reference, control values were established using whole human blood, at body temperature (37° C.), that had been re-calcified to a concentration of 10 mMol with anhydrous calcium chloride to reinstate clotting ability and to overwhelm the anticoagulant. The test volume was 27 µL; however, to ensure filling of the test chamber and complete immersion within the blood sample 50 of the wetted portion 24/plate 15 of the probe 20 disposed within the vial 15, a volume of 250 µL of blood was injected into a vial 15 comprising glass. Data recording began once the wetted portion 24/plate 15 was lowered into position such that it was immersed within the blood sample 50 and was 1 mm away from the lower member 50, both of which comprised acrylic. Deflection of the wire portion 21 of the probe 20 typically began after 360 to 480 seconds, and data collection was concluded after 3,600 seconds (1 hour).

To demonstrate the ability of the device to characterize clot elastic modulus (or stiffness) properties, after 3,600 seconds (1 hour), the piezoelectric adjustable positioning stage 23 was displaced vertically in an upward direction with micrometer precision and the resulting force imparted was translated to load, in a cantilevered mode, the wire portion 21 of the probe 20. This loading induced a tensile force in the clotting blood sample 50 that forms between the wetted portion 24/plate 15 and the lower member 31 within the vial 12. The resultant clot strain was detected as displacement of the flexible wire portion 21 resulting from contraction of the blood clot 50 and the force imparted to the probe 20, and images of the displacement were captured using a Hitachi® camera and was recorded at 10 micron intervals. The resultant clot stress was calculated based on the surface area of the wetted portion 24/plate 15 and the force imparted to the wire portion 21 of the probe 20 resulting from the upwards displacement of the piezoelectric adjustable positioning stage 23. The slope of the stress versus strain curves were then calculated and the data are presented in line 40 in FIG. 31, which illustrates the relationship between the derived displacement of the cantilevered wire portion 21 of the probe 20 of the apparatus 10 of FIGS. 5, 7 and 28-30, in microns, versus displacement sensed by the piezoelectric adjustable positioning stage 23, in microns.

Figure 31:
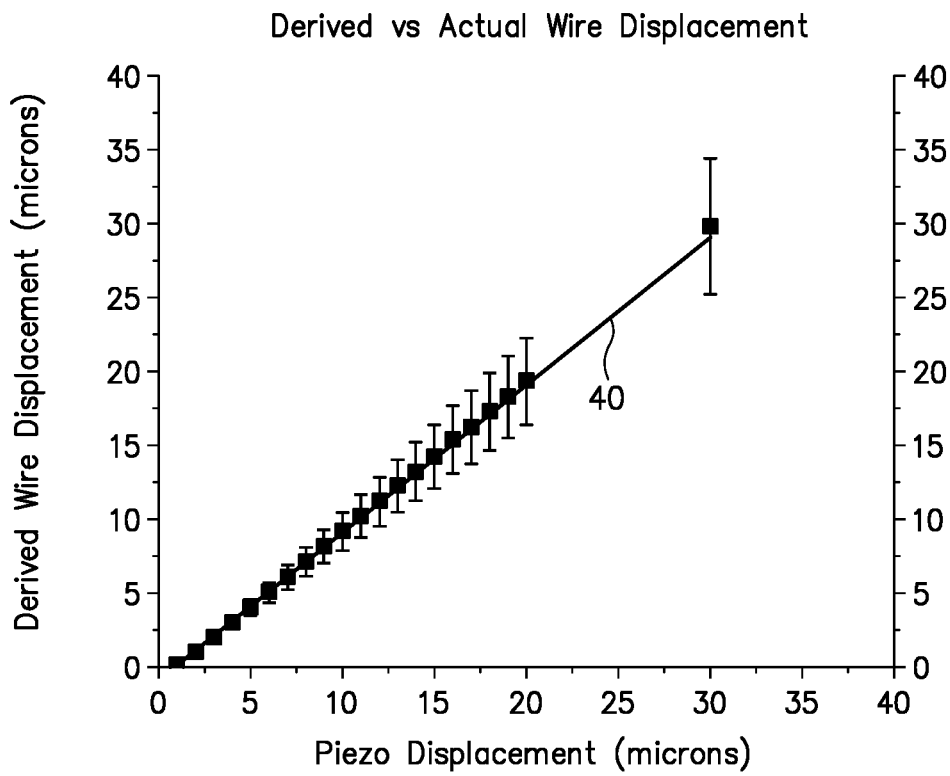
FIG. 31 is a plot of derived displacement of the wire portion of the probe of the embodiment of the apparatus of FIG. 30 versus displacement sensed by the piezoelectric adjustable positioning stage.

It was then demonstrated that the displacement of the wire portion 21 of the probe 20, in the cantilevered mode illustrated in the referenced drawings, reliably identifies clot contraction forces resulting from platelet activity within the contracting clotting blood sample 50. The correlation between the displacement induced by the piezoelectric adjustable positioning stage 23 and the derived displacement of the wire portion 21 of the probe 20 based on force as detected by the MEMS device 19 type displacement/force sensor is shown in FIG. 31. This value was obtained 5 times, each time using a new probe 20. The derived displacement of the wire portion 21 of the probe 20 is represented on the y-axis and was calculated from the force recorded by the MEMS device (force sensor) 19 using the equation provided above. Each derived displacement corresponded to an actual displacement set by the piezoelectric adjustable positioning stage 23. The relation between cantilevered deflection of the wire portion 21 of the probe 20 and energy elastically stored in the deflected wire portion 21 of the probe 20 as a result of the application of force to the probe 20 by contraction of the clotting blood sample 50 was linear, as seen in FIG. 31. Variation in the derived wire displacement increased at a rate of about 0.15 microns per micron of deflection of the wire portion 21 of the probe 20. The linear conformance of the curve was excellent with $R^2=0.999$. The maximum standard deviation observed, even at 30 microns of displacement, was 4.6 microns, or 15.3%. This illustrates that the cantilever equation given above is valid within the range of expected deflection that would result from a contracting blood sample 50. It was also confirmed that actual and predicted displacement of the wire portion 21 of the probe 20 was equal and within the expected range of variation. Induced deflection in the wire portion 21 of the probe 20 was elastic as there was no evidence of creep after the wire portion 21 of the probe 20 had been cycled four times from 0 to 30 microns.

Figure 32:
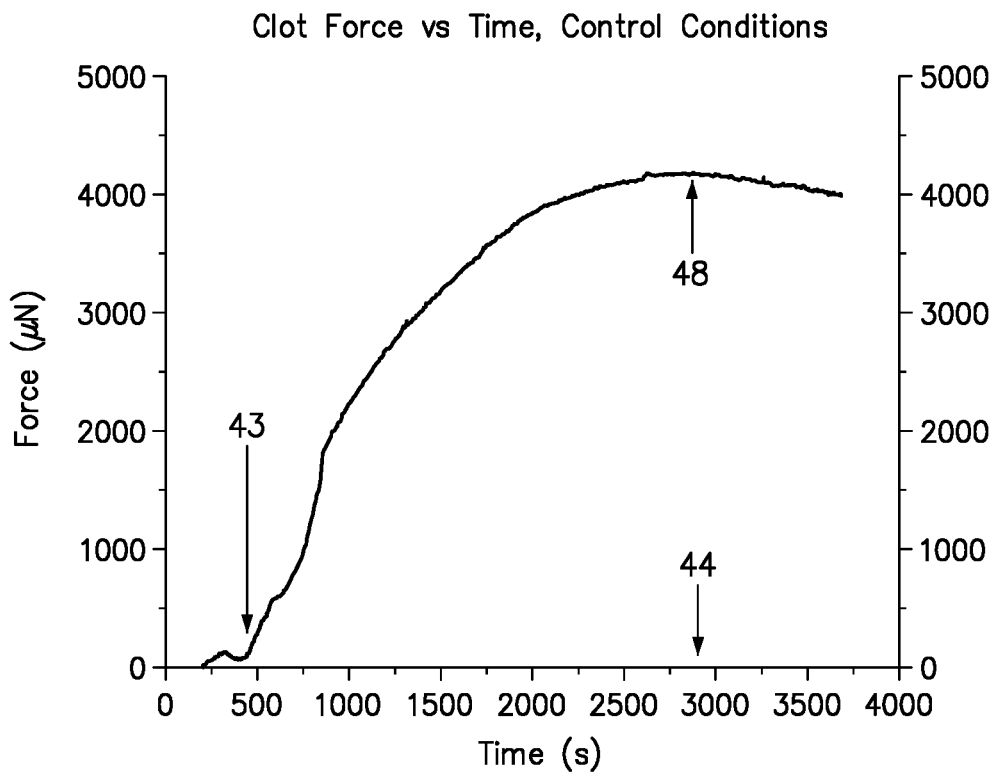
FIG. 32 is a graph of the contraction signal generated by the MEMS device of FIG. 31 to indicate the force applied by a contracting blood sample to the wetted portion of the probe, versus time, in seconds, for human whole blood samples analyzed in an embodiment of the apparatus of the present invention.

FIG. 32 is a graph of the contraction signal, which is the force applied by the contracting blood sample 50 to the probe 20, versus time, in seconds, for human whole blood samples analyzed in an embodiment of the apparatus 10 of the present invention. The exemplary embodiment of the apparatus 10 (see FIG. 30) was used to produce the contraction signal shown in FIG. 32. The same metrics were determined for the following sample assays and, as a group, represent standard ranges of such values for human whole blood samples 50 obtained from healthy persons. In the absence of a clotting blood sample 50 within the embodiment of the apparatus 10 of the present invention, there was a baseline amount of noise in the deflection signal identified as 1 micron, or approximately 130 µN. As shown on FIG. 31, the lift-off time (LT) 43 is on FIG. 32 indicates when platelet contraction begins, and was defined as when the recorded deflection signal exceeds the baseline noise (1 micron). Using this embodiment of the apparatus 10 of the present invention to characterize whole human blood, the lift-off time (LT) occurred at about 462 seconds and the rate of contraction (ROC) was about 4.27 µN/s. Ultimately, the clotting blood sample 50 imparted a maximum contraction force (MCF) 48 of 4,181 µN and the corresponding time-to-maximum (TTM) contraction force 44 was 2,886 seconds.

Figure 33:
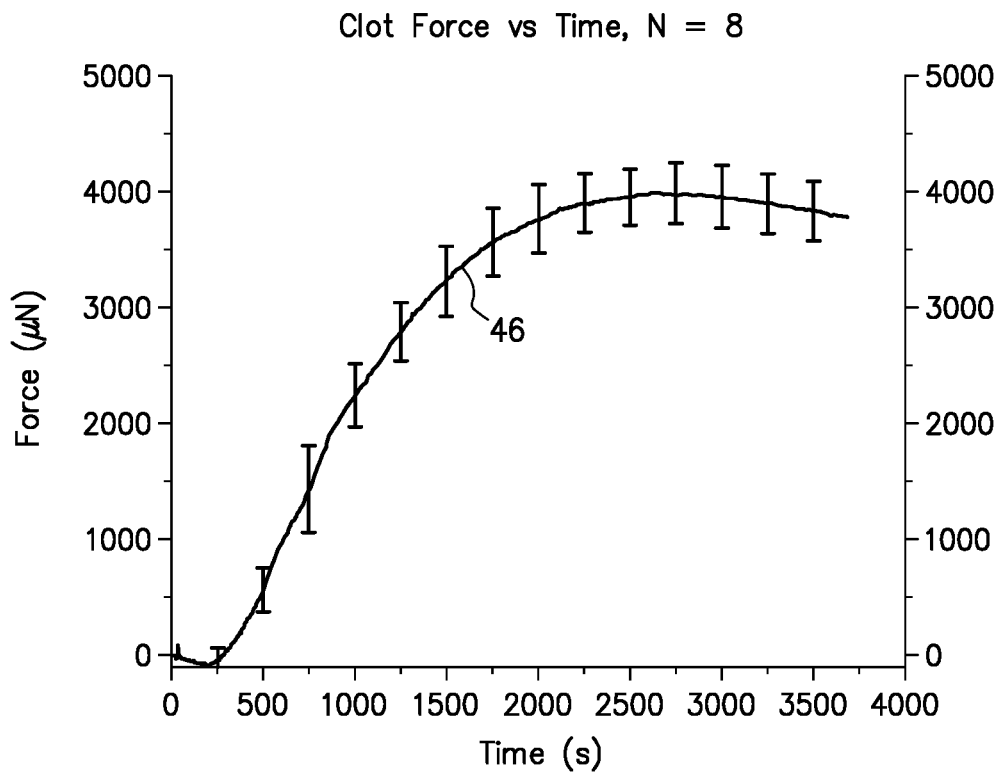
FIG. 33 is a graph of the force, in micronewtons, imparted to a wetted portion of a probe (shaped like a plate shown in FIG. 29) by the clotting blood sample disposed intermediate the plate and a lower member of the embodiment of the apparatus illustrated in FIG. 29 versus time, in seconds.

FIG. 33 is a graph of the force, in micronewtons, imparted to the plate 15 by the clotting blood sample 50 disposed intermediate the plate 15 and the lower member 31 of the embodiment of the apparatus 10 illustrated in FIG. 29 versus time, in seconds. This graph reflects the data obtained during tests designed to gauge the reproducibility of the data obtained using embodiments of the apparatus 10. Human whole blood from a single donor was analyzed eight times. The conditions included a temperature of 37° C., 10 mMol of CaCl, and 1 mm of separation between the plate 15 and the lower member 31 of the embodiment of the apparatus 10 (see FIG. 29) where the blood sample 50 is disposed for the test. The platelet count of the blood donor's samples averaged 213,000 platelets/µL. The graph of FIG. 33 illustrates the results of the tests. These assays were run in a single day and within 9 hours of collection of the blood samples 50 from the blood donor. Increases in blood sample 50 storage time were determined to result in no significant change in platelet contraction kinetics as determined using an embodiment of the inventive apparatus 10. For a single donor sample, the platelet contraction curve was found to be highly repeatable, with an average standard deviation for the eight assays of ±7.2%. As can be seen on FIG. 33, the observed lift-off time (LT) was 450 seconds, ROC was 3.4 µN/s, and maximum contraction force (MCF) was 3,995 µN and time to maximum was 2,643 s.

Figure 34:
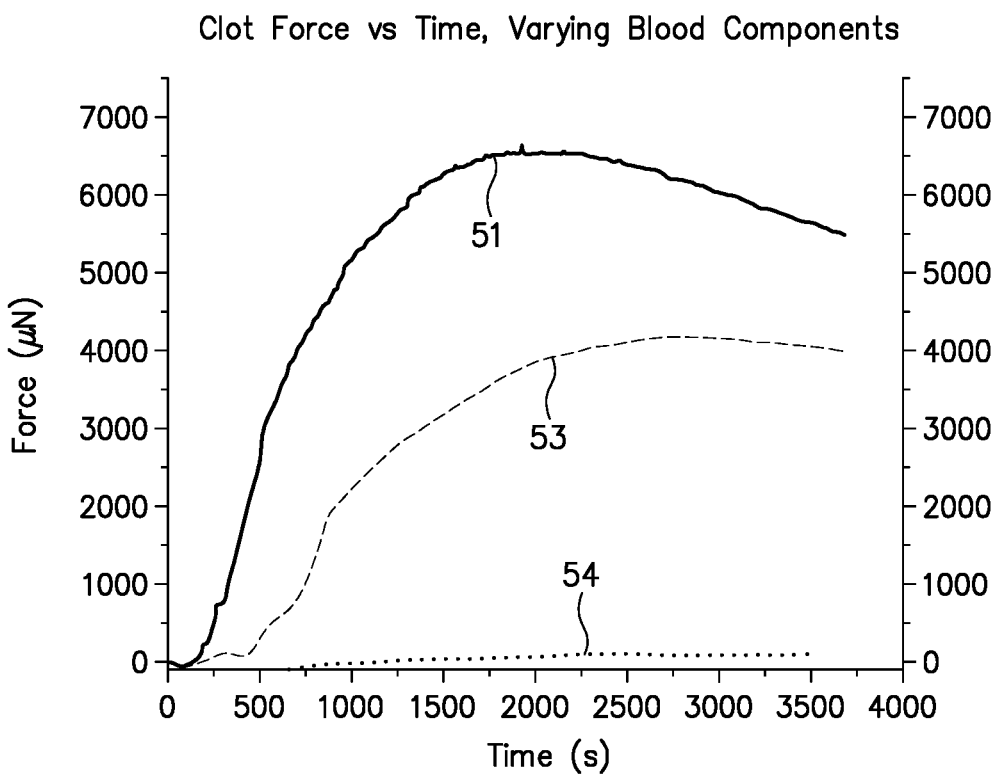
FIG. 34 is a graph of the force imparted by a clotting blood sample to the probe versus time, in seconds, for blood samples containing varying components that influence the clotting of the blood sample.

FIG. 34 is a graph of the force imparted by a clotting blood sample 50 to the probe 20, in micronewtons, versus time, in seconds, for blood samples containing varying components. This graph illustrates the effect of the variance in blood components of the blood samples 50 tested using an embodiment of the apparatus 10 of the present invention. More specifically, the blood samples 50 tested to obtain the data reflected in FIG. 34 varied by platelet concentrations, with a blood sample 50 of whole human blood having a platelet count of 195,000 platelets/µL (observed data illustrated by line 53), a platelet-rich plasma with a platelet count of 200,000 platelets/µL (line 51) and platelet-poor plasma with only 20 platelets/µL (line 54). These assays were run at 37° C. with 10 mMol concentration of CaCl.

As indicated by line 51 of FIG. 34, blood clots resulting from platelet-rich plasma blood samples 50 generated higher contraction forces than the contraction forces for whole human blood, which corresponds to line 53 of FIG. 34. Even when adjusted for platelet count, the blood samples 50 with platelet-rich plasma (line 51) generated a stronger contraction signal in less time (6,646 µN in 1,926 s) as compared to that generated by whole human blood (line 53) (4,181 µN in 2,886 s). Blood clots in platelet-rich plasma contracted earlier, as characterized by the leftmost lift-off time (LT) of the line 51, and faster, as characterized by rate of contraction (ROC), than did the clotting whole human blood, line 53. Platelet-rich plasma clotting also generated a signal lift-off time (LT) at 186 seconds with a rate of contraction (ROC) of 4.47 µN/s, while the whole blood lift-off time (LT) was 462 s with a rate of contraction (ROC) of 4.27 µN/s). As was anticipated, little or no significant clot contraction force was detected in the platelet-poor plasma blood sample, reflected in line 54. FIG. 34 demonstrates the capacity of embodiments of the apparatus 10 of the present invention to reliably characterize the effect of platelet count on the contraction forces generated by clotting human blood.

Figure 35:
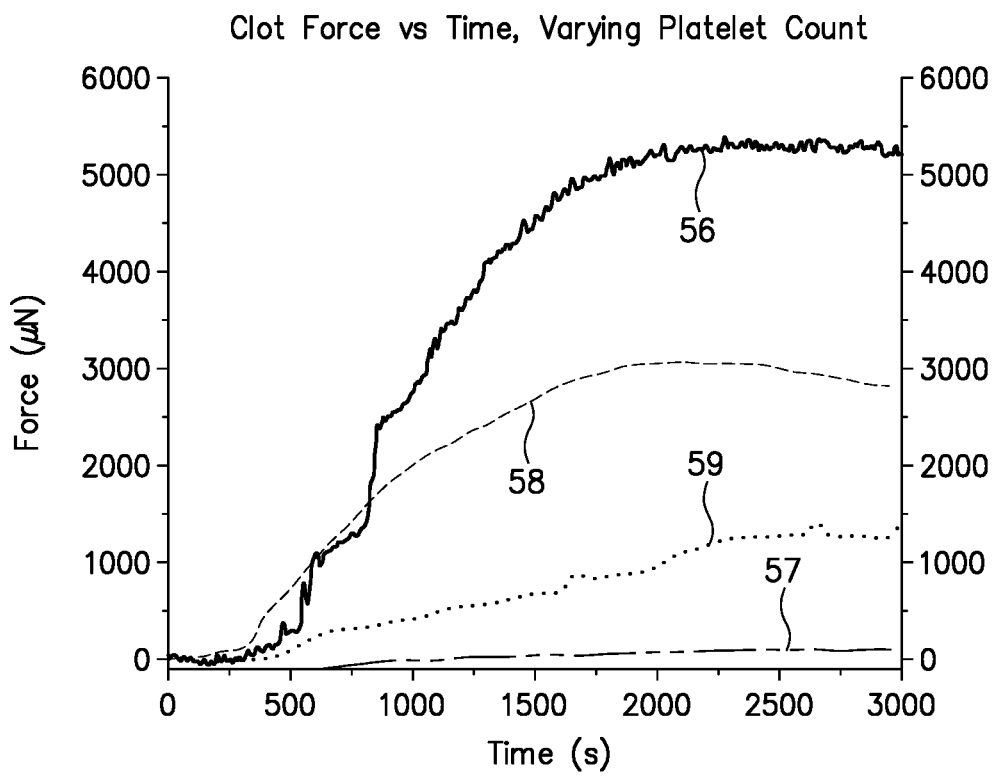
FIG. 35 is a graph illustrating the effects of dilution of human whole blood samples having a platelet count of 195,000 platelets/μL with platelet-poor plasmas of varying platelet counts.

FIG. 35 is a graph illustrating the effects of dilution of human whole blood samples 50 having a platelet count of 195,000 platelets/µL with platelet-poor plasmas of varying platelet counts. Included in the graph of FIG. 35 to enable comparison is a solid line 56 reflecting the data obtained from testing an undiluted human whole blood sample 50 having 195,000 platelets/µL. The remaining three lines reflect the data obtained as a result of further testing of three differing diluted human whole blood samples 50, each human whole blood sample being diluted with platelet-poor plasma with a platelet count of only 1,000 platelets/µL. More specifically, a first aliquot of human whole blood sample 50 was diluted by 50% (e.g., one part human whole blood and one part platelet-poor plasma) with platelet-poor plasma to produce a blood sample having 96,000 platelets/µL (line 58), a second human whole blood sample 50 was diluted by 75% (e.g., one part human whole blood and three parts platelet-poor plasma) with platelet-poor plasma to produce a blood sample having 50,000 platelets/µL (line 59) and a third sample consisting of the platelet-poor plasma (see above—having only 1,000 platelets/µL) (line 57). The resulting clot contraction forces were linearly related to the platelet count. The first aliquot (line 58) resulted in a 55% reduction in the maximum contraction force (MCF) as compared to the undiluted human whole blood sample and in a rate of contraction (ROC) decreased by 51%. The second aliquot (line 59) resulted in a 75.8% reduction in maximum contraction force (MCF) and in a rate of contraction (ROC) decreased by 89%. In the first aliquot, the lift-off time (LT) was not significantly different from that of undiluted whole blood. However, in the second aliquot, the lift-off time (LT) was prolonged to 528 seconds. Neither the 50% nor the 75% dilution demonstrated a change in time-to-maximum (TTM) as compared to that observed in the undiluted whole blood sample.

Figure 36:
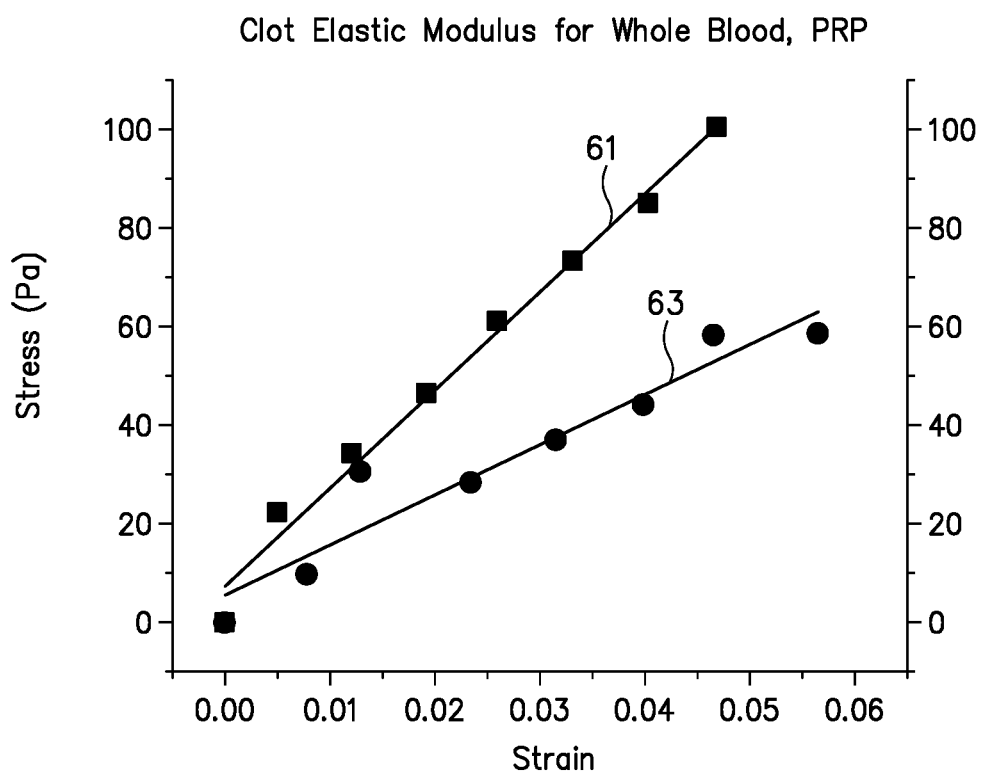
FIG. 36 is a graph of stress versus strain, indicating the elastic modulus for samples of clotting human whole blood.

FIG. 36 is a graph of stress versus strain, indicating the elastic modulus for clotted human blood. FIG. 36 illustrates data relating to the effect of varying concentrations of red blood cells (erythrocytes) within a human whole blood sample 50 (line 63) and within a platelet-rich plasma (line 61) on the elastic modulus as determined using an embodiment of the apparatus 10 of the present invention. The data was obtained after completion of the clot contraction force assay by application of tensile stress to the clotted blood samples 50 via the flexible wire portion 21 of the probe 20 resulting in the upward translation of the piezoelectric adjustable positioning stage 23. The resulting strain was calculated based on upward expansion of the clotting blood sample 50 and the height of the clotted blood sample 50 after contraction from a starting height of 1 mm. As shown by FIG. 36, the elastic modulus of the clotted blood sample formed by human whole blood having a platelet count of 190,000 platelets/µL was 1991 pascals, the elastic modulus of the clotted platelet-rich plasma having a platelet count of 200,000 platelets/µL was 1015 pascals. FIG. 36 demonstrates that embodiments of the apparatus 10 of the present invention were used to obtain data showing that the increase in the presence of red blood cells during clot formation enhanced the elastic modulus of the blood clot and thus the strength of the blood clot.

Figure 37:
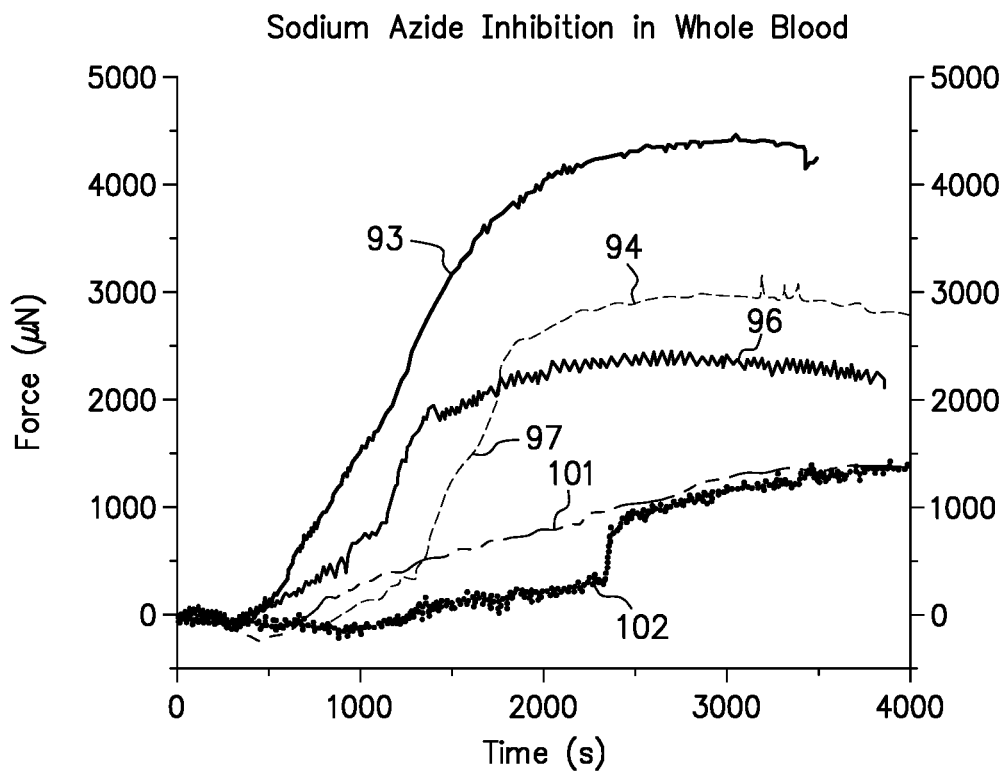
FIG. 37 is a graph illustrating the capacity of embodiments of the apparatus of the present invention to characterize metabolic dysfunction in human whole blood caused by various concentrations of sodium azide.

FIG. 37 is a graph illustrating the capacity of embodiments of the apparatus of the present invention to characterize metabolic dysfunction in human whole blood caused by various concentrations of sodium azide. An embodiment of the apparatus 10 of the present invention was used to gauge the impact of the varying concentrations of sodium azide in human whole blood, and the data obtained establishes the capacity of the apparatus 10 to identify and characterize the effect of varying concentrations of this inhibitor on normal platelet metabolic function. Clinically relevant correlations were possible with the apparatus as well.

For example, but not by way of limitation, sodium azide is an inhibitor of complex IV in the electron transport chain that disrupts the mitochondrial oxidative phosphorylation. When sodium azide is added to a human whole blood sample, it reduces measured platelet respiration in a dose-dependent fashion. In a clinical observation, this mode of inhibition parallels that seen in Alzheimer's disease where levels of complex IV in the platelet mitochondria are significantly reduced (Valla, J., et al., *Impaired platelet mitochondrial activity in Alzheimer's disease and mild cognitive impairment*; Mitochondrion, 2006. 6(6): p. 323-30). Similarly, use of an embodiment of the apparatus 10 of the present invention enabled the dose-dependent reduction in contraction forces associated with increasing concentrations of sodium azide to be quantified.

FIG. 37 includes line 93, which corresponds to the contraction force of a human whole blood sample without sodium azide. Line 96 corresponds to the reduced contraction force resulting from a sodium azide concentration of 10 mMol in the blood. Line 94 corresponds to the reduced contraction force resulting from a sodium azide concentration of 50 mMol in the blood. Line 101 corresponds to the reduced contraction force resulting from a sodium azide concentration of 25 mMol in the blood. Line 102 corresponds to the reduced contraction force resulting from a sodium azide concentration of 100 mMol.

Figure 38:
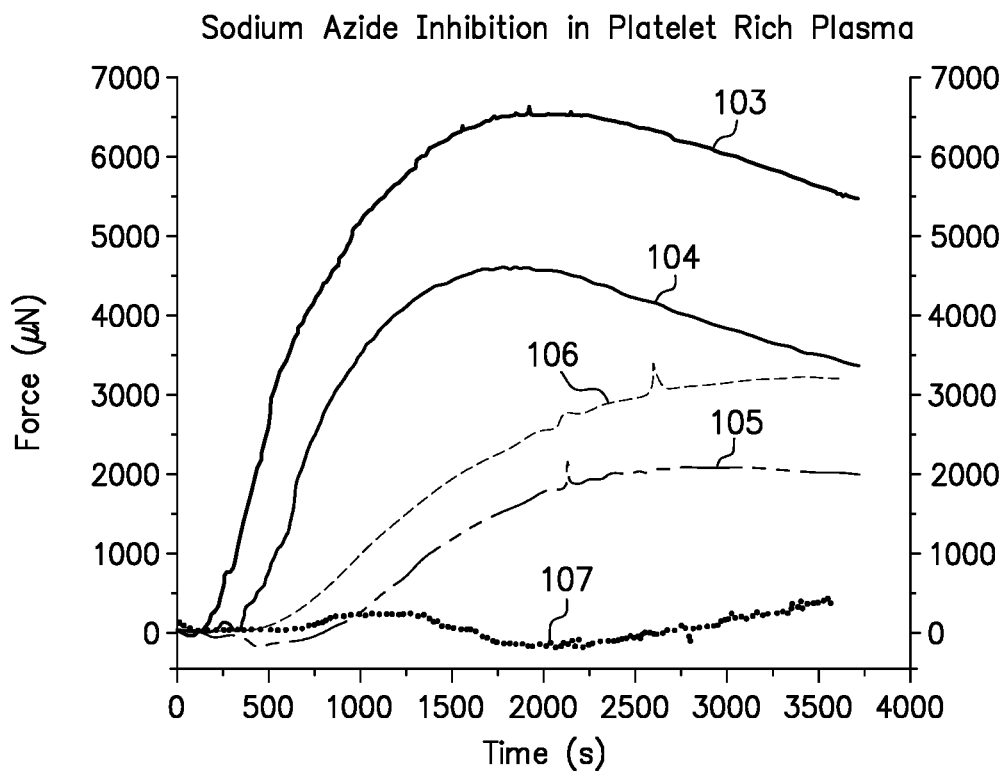
FIG. 38 is a graph illustrating the capacity of embodiments of the apparatus of the present invention to characterize metabolic dysfunction in platelet-rich plasma caused by various concentrations of sodium azide discussed above in relation to FIG. 37.

FIG. 38 is a graph illustrating the capacity of embodiments of the apparatus of the present invention to characterize metabolic dysfunction in platelet-rich plasma caused by various concentrations of sodium azide discussed above in relation to FIG. 37. FIG. 38 includes line 103, which corresponds to the contraction force of the platelet-rich plasma sample without sodium azide. Line 104 corresponds to the reduced contraction force resulting from a sodium azide concentration of 1 mMol in the platelet-rich plasma. Line 106 corresponds to the reduced contraction force resulting from a sodium azide concentration of 50 mMol in the platelet-rich plasma. Line 105 corresponds to the reduced contraction force resulting from a sodium azide concentration of 10 mMol in the platelet-rich plasma. Line 107 corresponds to the reduced contraction force resulting from a sodium azide concentration of 100 mMol in the platelet-rich plasma.

Cytochalasins inhibit the mechanical process of actin polymerization and produce a dose-dependent decrease in measured platelet contraction forces. This effect is clinically similar to that which occurs in patients with Wiskott-Aldrich syndrome and which exhibit mild thrombocytopenia with impaired movements of actin filaments in the cytoskeleton. A number of studies demonstrate that exposure to cytochalasin reduces both the rate and amount of platelet contraction. Platelet overall clot strength after formation was also reduced as was elastic modulus, a measure of clot strength. When cytochalasin D was added to whole blood, an embodiment of the apparatus 10 detected a dose-dependent decrease in clotting force of contraction associated with increasing concentrations of cytochalasin D (e.g., 0.1 uMol, 0.5 uMol, 1 uMol, 50 uMol and 50 uMol) in a whole blood sample.

Figure 39:
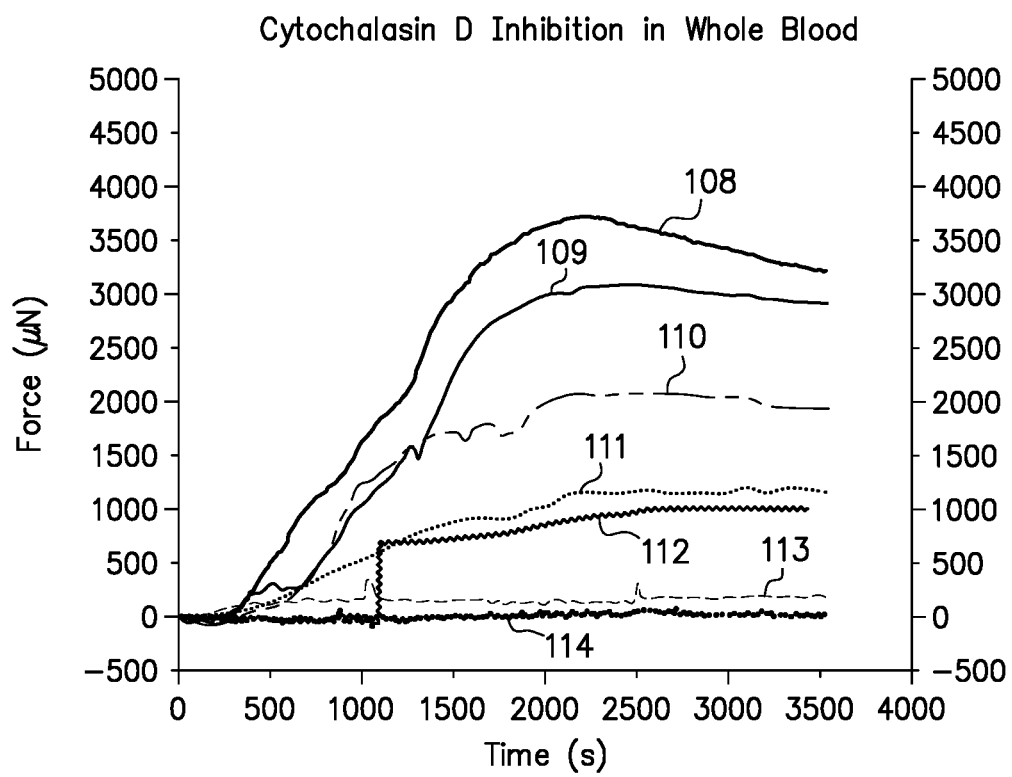
FIG. 39 is a graph illustrating the capacity of embodiments of the apparatus of the present invention to characterize metabolic dysfunction in human whole blood caused by various concentrations of cytochalasin D.

FIG. 39 is a graph illustrating the capacity of embodiments of the apparatus of the present invention to characterize metabolic dysfunction in human whole blood caused by various concentrations of cytochalasin D. Line 109 to the reduced contraction force resulting from a dimethyl sulfoxide (DMSO) 0.02% concentration in the human whole blood. Line 110 of FIG. 39 corresponds to a cytochalasin D concentration of 0.1 µMol. Line 111 corresponds to a cytochalasin D concentration of 0.5 µMol. Line 111 corresponds to a cytochalasin D concentration of 0.5 µMol. Line 112 corresponds to a cytochalasin D concentration of 1 µMol. Line 113 corresponds to a cytochalasin D concentration of 5 µMol. Line 114 corresponds to a cytochalasin D concentration of 50 µMol.

Sodium cyanide is a potent inhibitor of respiration, acting on mitochondrial cytochrome oxidase and uncoupling electron transport resulting in decreased mitochondrial oxidative metabolism. When cyanide was added to whole blood the apparatus 10 of the present invention was able to detect a dose-dependent decrease in clotting force of contraction associated with increasing concentrations of cyanide.

Figure 40:
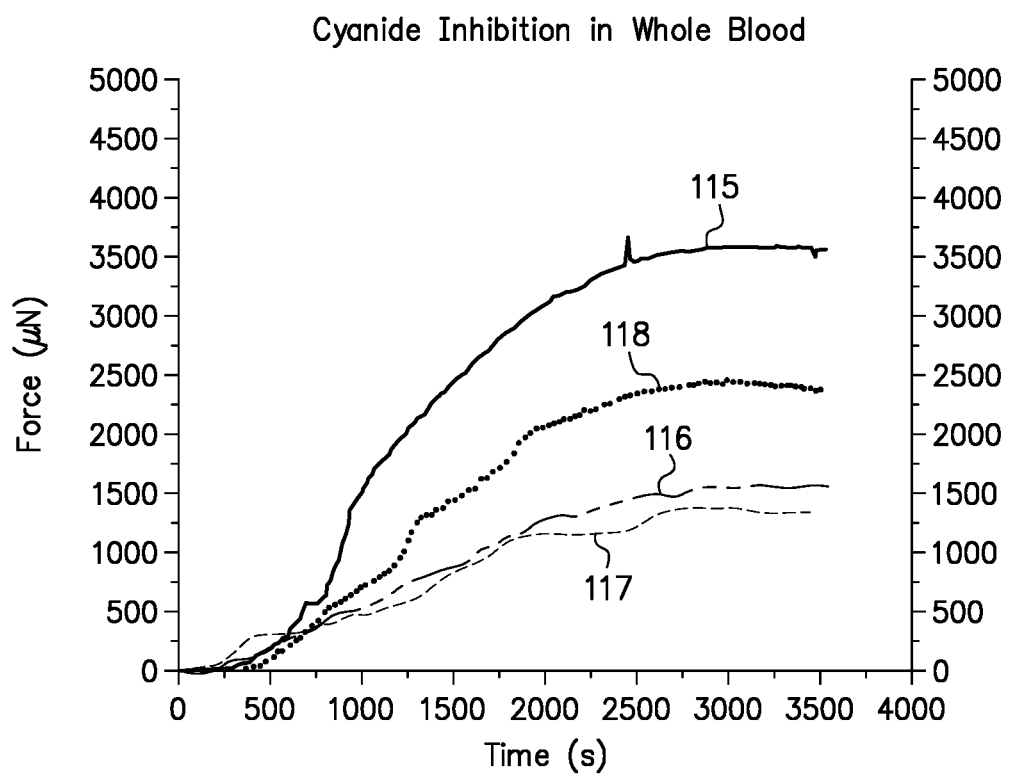
FIG. 40 is a graph illustrating the capacity of embodiments of the apparatus of the present invention to characterize metabolic dysfunction in human whole blood caused by various concentrations of cyanide.

FIG. 40 is a graph illustrating the capacity of embodiments of the apparatus of the present invention to characterize metabolic dysfunction in human whole blood caused by various concentrations of cyanide. Line 115 corresponds to human whole blood without cyanide. Line 116 to the reduced contraction force resulting from a concentration of 10 µMol cyanide in the human whole blood. Line 118 to the reduced contraction force resulting from a concentration of 100 µMol cyanide in the human whole blood. Line 117 to the reduced contraction force resulting from a concentration of 25 µMol cyanide in the human whole blood.

Tetrazolium dye MTT 3-(4,5-dimethylthiazol-2-yl)-2,5-diphenyltetrazolium bromide reduction is dependent on NAD(P)H-dependent oxidoreductase enzymes. Therefore, reduction of MTT and other tetrazolium dyes depends on the cellular metabolic activity due to NAD(P)H flux which causes a change in color, which is the basis of the MTT assay. The MTT assay is used as a colorimetric assay for assessing cell metabolic activity.

Figure 41:
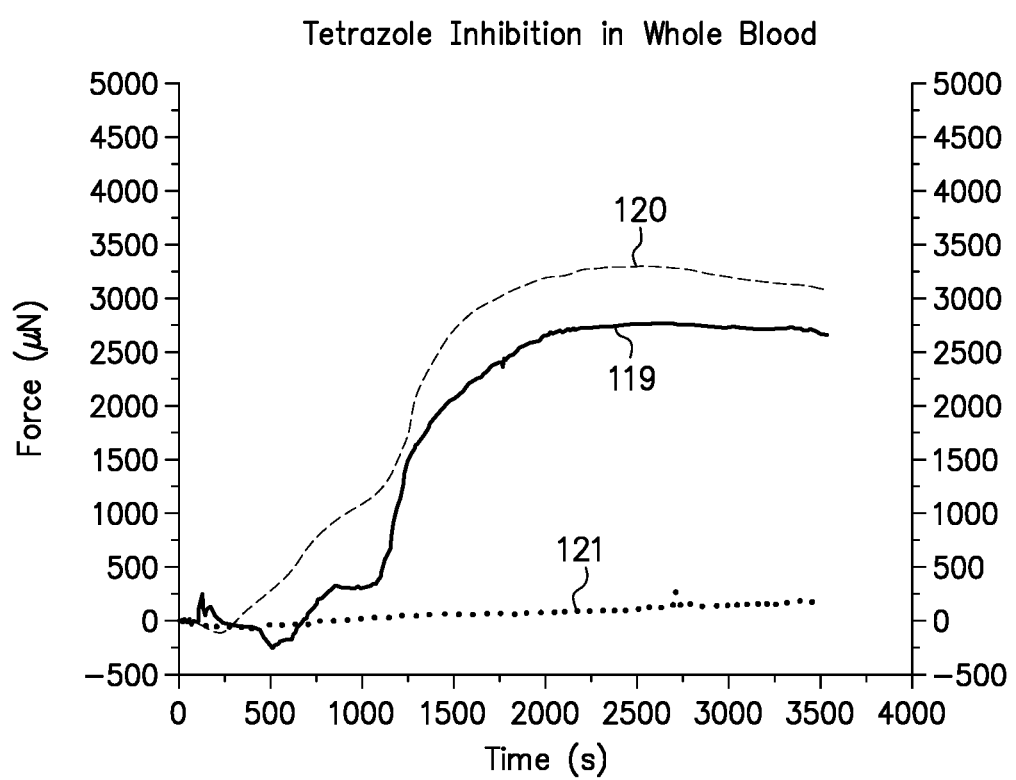
FIG. 41 is a graph illustrating the capacity of embodiments of the apparatus of the present invention to characterize metabolic dysfunction in human whole blood caused by various concentrations of tetrazole.

FIG. 41 is a graph illustrating the capacity of embodiments of the apparatus of the present invention to characterize metabolic dysfunction in human whole blood caused by various concentrations of tetrazole. Line 120 corresponds to the enhanced contraction force resulting from a concentration of 1 mMol of tetrazole in human whole blood. Line 121 corresponds to the reduced contraction force resulting from a concentration of 60 mMol in human whole blood.

Embodiments of the method of the present invention provide for detecting a decrease in the forces generated within a blood sample obtained from a patient that result from energy dysfunction. Cells make energy by using adenosine triphosphate (ATP), often referred to as the "molecular unit of currency." There are two ways in which ATP can be used in a cell to make energy. These are referred to as glycolysis and oxidative phosphorylation. The loss of energy due to mitochondrial dysfunction reduces the capacity of the blood to clot and thereby reduces the capacity of the clotting blood sample to impart forces to a probe of an embodiment of the apparatus 10 of the present invention.

Sepsis results in a number of anomalies and pathologies, one of which is mitochondrial dysfunction. Mitochondrial dysfunction is an indirect indicator of sepsis and is detectable, using embodiments of the apparatus 10 and method of the present invention, earlier than other manifestations of the condition thereby enabling the condition to be addressed through patient treatment at a much earlier stage, which can be critical.

Figure 42:
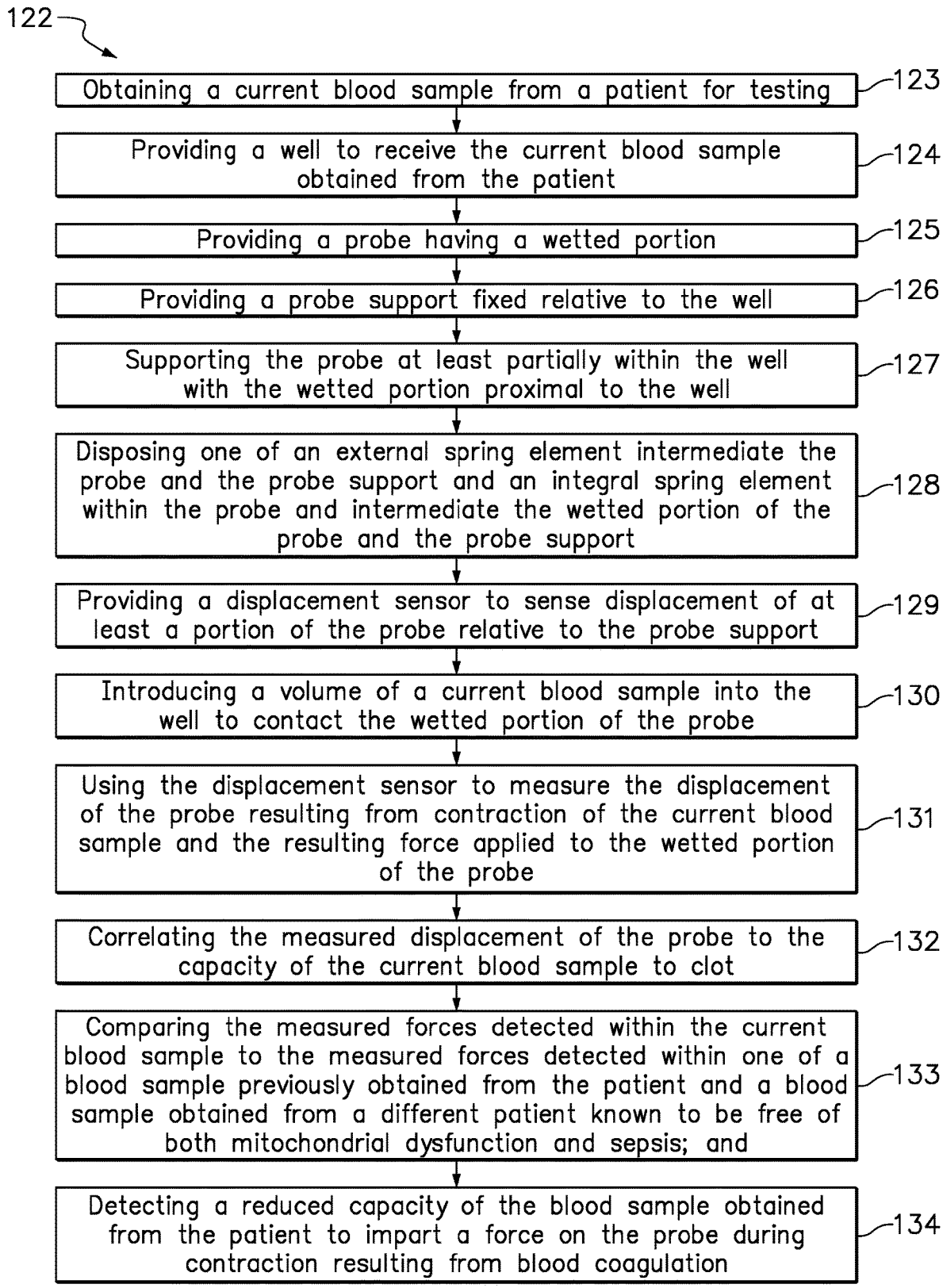
FIG. 42 is a high-level flowchart illustrating the steps of an embodiment of a method of the present invention for detecting a reduction in the contraction force imparted to a probe having a wetted portion contacted by a sample of blood obtained from a patient.

FIG. 42 is a high-level flowchart illustrating the steps of an embodiment of a method 122 of the present invention for detecting a reduction in the contraction force imparted to a probe having a wetted portion contacted by a sample of blood obtained from a patient. The purpose of the embodiment of the method 122 is to provide an indication of mitochondrial dysfunction in the obtained blood sample that indicates a blood condition such as, for example, sepsis or some other condition that relates to or may cause mitochondrial dysfunction. In step 123, a current blood sample is obtained from a patient for testing. In step 124, a well to receive the current blood sample obtained in step 123 is provided. In step 125, a probe having a wetted portion is provided. In step 126, a probe support fixed relative to the well is provided. In step 127, the probe is supported using the probe support with at least a portion (the wetted portion) proximal to the well. This step enables the wetted portion of the probe to be contacted by the current blood sample obtained from the patient as will be discussed below. In step 128, one of an external spring element and a spring element that is integral with the probe is disposed intermediate the wetted portion of the probe and the probe support. In step 129, a displacement sensor is provided to detect and measure displacement of at least a portion of the probe relative to the well and the probe support fixed relative to the well. In step 130, a volume of the current blood sample obtained from the patient is introduced into the well to contact the wetted portion of the probe. In step 131, the displacement sensor is used to measure the displacement of the probe resulting from the contraction of the current blood sample and the resulting force applied to the wetted portion of the probe. In step 132, the measured displacement of the probe is correlated to the capacity of the obtained blood sample to clot. In step 133, the measured capacity of the current blood sample to clot is compared to the capacity of one of a blood sample previously obtained from the patient and a blood sample obtained from another known to be free of mitochondrial dysfunction and sepsis to clot. Finally, in step 134, a reduced capacity of the obtained blood sample to clot is detected.

The capacity of embodiments of the apparatus and method of the present invention to identify alterations in clotting activity due to various metabolic inhibitors clearly demonstrates its utility in monitoring mitochondrial dysfunctions as manifested by platelet energetics and mechanics.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, components and/or groups, but do not preclude the presence or addition of one or more other features, integers, steps, operations, elements, components, and/or groups thereof. The terms "preferably," "preferred," "prefer," "optionally," "may," and similar terms are used to indicate that an item, condition or step being referred to is an optional (not required) feature of the invention.

As used herein, the term "patient" or "subject" refers to a living mammalian organism, such as a human or veterinary patient (such as, but not limited to non-human primates, companion animals (dog, cat, etc.), cow, sheep, goat and laboratory animals such as mouse, rat, guinea pig, etc. In certain embodiments, the patient or subject is a primate. Non-limiting examples of human subjects are adults, juveniles and infants.

It will be understood that the above discussion is isolated to human blood, but the findings and, in particular, the applications of embodiments of the inventive apparatus and method are applicable to the testing and analysis of blood of animals as well. It should be noted that, in human subjects, a normal platelet count ranges from 150,000 to 450,000 platelets per microliter of blood. Having more than 450,000 platelets is a condition called thrombocytosis, and having less than 150,000 is known as thrombocytopenia. For veterinary subjects a normal platelet count range will vary between genus and even species. For example, in dogs, a normal platelet count generally ranges from 200,000 to 900,000 platelets per microliter of blood and, in cats, a normal platelet count generally ranges from 300,000 to 700,000 platelets per microliter of blood.

The corresponding structures, materials, acts, and equivalents of all means or steps plus function elements in the claims below are intended to include any structure, material, or act for performing the function in combination with other claimed elements as specifically claimed. The description of the present invention has been presented for purposes of illustration and description, but it is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

We claim:

1. An apparatus (10) for use in determining the capacity of a blood sample (50) to clot, comprising:
   a well (30) to receive the blood sample;
   a probe support (29) fixed relative to the well;
   a probe (20) supported within the well on the probe support, the probe including a wetted portion (24) proximal to the well;
   a deformable spring element (35) coupled intermediate the wetted portion of the probe and the probe support; and
   a microelectromechanical displacement sensor (19) disposed on the apparatus to measure movement of the probe (20) the microelectromechanical displacement sensor being in engagement with the probe to detect and measure the displacing force imparted to the probe as a result of the contraction of the blood sample within the well;
   wherein the introduction of a volume of a blood sample (50) into the well (30) contacts the wetted portion (24) of the probe with the blood sample; and
   wherein the clotting and contraction of the blood sample (50) imparts a displacing force to the wetted portion of the probe and results in a displacement of the probe relative to the probe support.

2. The apparatus of claim 1, wherein the well (30) comprises an interior surface (32) conditioned to one of promote, alter and impair the adherence of the blood sample to the interior surface as the blood sample clots and contracts.

3. The apparatus of claim 1, wherein an exterior surface (22) of the wetted portion (24) of the probe is conditioned to one of promote, alter and impair adherence of the blood sample to the wetted portion of the probe as the blood sample clots and contracts.

4. The apparatus of claim 1, wherein the displacement of the probe (20) results in elastic deformation of the spring element.

5. The apparatus of claim 1, wherein the well is disposed on a tray that supports the probe support (29).

6. The apparatus of claim 1, wherein the probe (20) is pivotally coupled to the probe support (29).

7. The apparatus of claim 1, wherein the wetted portion (24) of the probe includes a radially enlarged portion (15).

8. The apparatus of claim 7, wherein the shape of the radially enlarged portion (15) of the wetted portion of the probe is one of bulbous, disc-shaped, rounded and frusto-conical.

9. The apparatus of claim 1 wherein the spring element (28A) is integral with the probe and is disposed intermediate the wetted portion (24) of the probe and the probe support (29).

* * * * *